US005703054A

United States Patent [19]
Bennett et al.

[11] Patent Number: 5,703,054
[45] Date of Patent: Dec. 30, 1997

[54] OLIGONUCLEOTIDE MODULATION OF PROTEIN KINASE C

[75] Inventors: C. Frank Bennett, Carlsbad; Nicholas Dean, Cardiff-by-the-Sea, both of Calif.

[73] Assignee: Isis Pharmaceuticals, Inc., Carlsbad, Calif.

[21] Appl. No.: 89,996

[22] Filed: Jul. 9, 1993

Related U.S. Application Data

[63] Continuation-in-part of Ser. No. 852,852, Mar. 16, 1992, abandoned.

[51] Int. Cl.$^6$ ............................................. A61K 31/70
[52] U.S. Cl. ..................... 514/44; 536/22.1; 536/23.1; 536/23.5; 536/24.1; 536/24.2; 536/24.3; 536/24.31; 536/25.1; 536/25.2; 536/25.3; 536/25.31; 935/6; 935/8; 935/9; 935/10; 935/11; 435/194
[58] Field of Search ........................... 514/44; 536/22.1, 536/23.1, 23.5, 24.1, 24.2, 24.3, 24.31, 25.1, 25.2, 25.3, 25.31; 935/6, 8, 9, 10, 11; 435/194

[56] References Cited

U.S. PATENT DOCUMENTS

| | | | |
|---|---|---|---|
| 4,511,713 | 4/1985 | Miller et al. | 435/6 |
| 5,034,506 | 7/1991 | Summerton et al. | 528/391 |
| 5,098,890 | 3/1992 | Gewirtz et al. | 514/44 |
| 5,138,045 | 8/1992 | Cook et al. | 536/24.5 |

OTHER PUBLICATIONS

Bacher et al., "Isolation and Characterization of PKC-L, A New Member of the Protein Kinase C-Related Gene Family Specifically Expressed in Lung, Skin, and Heart", *Molecular and Cellular Biology* 11: 126–133 (1991).

Ballester and Rosen, "Fate of Immunoprecipitable Protein Kinase C in GH$_3$ Cells Treated with Phorbol 12-Myristate 13-Acetate", *Journal of Biological Chemistry* 260: 15194–15199 (1985).

Coussens et al., "Multiple, Distinct Forms of Bovine and Human Protein Kinase C Suggest Diversity in Cellular Signaling Pathways", *Science* 233: 859–866 (1986).

Endo et al., "Cell Membrane Signaling as Target in Cancer Therapy: Inhibitory Effect of N,N-Dimethyl and N,N,N-Trimethyl Sphingosine Derivatives on in Vitro and in Vivo Growth of Human Tumor Cells in Nude Mice", *Cancer Research* 51: 1613–1618 (1991).

Finkenzeller et al., "Sequence of Human Protein Kinase C α", *Nucl. Acids Res.* 18: 2183 (1990).

Gescher and Dale, "Protein Kinase C—A Novel Target for Rational Anti-Cancer Drug Design?", *Anti-Cancer Drug Design* 4: 93–105 (1989).

Godson et al., "Inhibition of Expression of Protein Kinase C α By Antisense cDNA Inhibits Phorbol Ester-Mediated Arachidonate Release", *J. Biol. Chem.* 268: 11946–11950 (1993).

Hegemann and Mahrle, "Biochemical Pharmacology of Protein Kinase C and Its Relevance for Dermatology", *Pharmacology of the Skin*, H. Mukhtar, ed., CRC Press, Boca Raton, FL 357–368 (1992).

Hidaka and Hagiwara, "Pharmacology of the Isoquinoline Sulfonamide Protein Kinase C Inhibitors", *Trends in Pharm. Sci.* 8: 162–164 (1987).

Krug et al, "Evidence for Increased Synthesis as Well as Increased Degradation of Protein Kinase C After Treatment of Human Osteosarcoma Cells with Phorbol Ester", *J. Biol. Chem.* 262: 11852–11856 (1987).

Kubo et al., "Primary Structures of Human Protein Kinase CβI and βII Differ Only in their C-Terminal Sequences", *FEBS Lett.* 223: 138–142 (1987).

Nishizuka, "The Molecular Heterogeneity of Protein Kinase C and Its Implications for Cellular Regulation", *Nature* 334: 661–665 (1988).

Nielsen et al., "Sequence-Selective Recognition of DNA by Strand Displacement with a Thymine-Substituted Polyamide", *Science* 254: 1497–1500 (1991).

Osada et al., "A Phorbol Ester Receptor/Protein Kinase, nPKCη, a New Member of the Protein Kinase C Family Predominantly Expressed in Lung and Skin", *J. Biol. Chem* 265: 22434–22440 (1990).

Parker et al., "The Complete Primary Structure of Protein Kinase C–the Major Phorbol Ester Receptor", *Science* 233: 853–866 (1986).

Rothenberg et al, "Oligodeoxynucleotides as Anti-Sense Inhibitors of Gene Expression: Therapeutic Implications", *J. Natl. Cancer Inst.* 81: 1539–1544 (1989).

Sakanoue et al., "Protein Kinase C Activity as Marker for Colorectal Cancer", *Int. J. Cancer* 48: 803–806 (1991).

Weinstein et al., "Cancer Prevention: Recent Progress and Future Opportunities", *Cancer Res.* (Suppl.) 51: 5080s–5085s (1991).

Young et al., "Down-Regulation of Protein Kinase C is Due to an Increased Rate of Degradation", *Biochem. J.* 244: 775–779 (1987).

Zon, "Oligonucleotide Analogues as Potential Chemotherapeutic Agents", *Pharmaceutical Res.* 5: 539–549 (1988).

(List continued on next page.)

*Primary Examiner*—Christopher S. F. Low
*Attorney, Agent, or Firm*—Woodcock Washburn Kurtz Mackiewicz & Norris, LLP

[57] ABSTRACT

Compositions and methods are provided for the treatment and diagnosis of diseases associated with protein kinase C. Oligonucleotides are provided which are specifically hybridizable with nucleic acid encoding PKC. Oligonucleotides specifically hybridizable with a translation initiation site, 5'-untranslated region or 3'-untranslated region are provided. Oligonucleotides specifically hybridizable with a particular PKC isozyme or set of isozymes are also provided. Methods of treating animals suffering from disease amenable to therapeutic intervention by modulating protein kinase C expression with an oligonucleotide specifically hybridizable with RNA or DNA corresponding to PKC are disclosed.

21 Claims, 13 Drawing Sheets

OTHER PUBLICATIONS

Borek et al., "Long-Chain (sphingoid) Bases Inhibit Multistage Carcinogenesis in Mouse C3H/10T1/2 Cells Treated with Radiation and Phorbol 12-Myristate 13-Acetate", *Proc. Natl. Acad. Sci.* 88:1953–1957 (1991).

Marcus-Sekura, "Techniques for Using Antisense Oligodeoxyribonucleotides to Study Gene Expression", *Analytical Biochemistry* 172: 289–295 (1988).

*Webster's II New Riverside University Dictionary*, Soukkhanov et al. (eds.) 1984, Houghton Mifflin Company, Boston, MA p. 68.

Watson et al. 1987, in: *Molecular Biology Of The Gene*, fourth edition, Benjamin/Cummings Publishing Company, Menlo Park, CA, p. 241.

Kawasaki et al. 1991 (January) "Synthesis and Biophysical Studies of 2'-dRIBO-F Modified Oligonucleotides", Conference on Nucleic Acid Therapeutics, Clearwater, FL.

Berkowitz et al., 1973 J. Medicinal Chemistry, 16(2):813–814.

Standaert et al., 1991, J. Cellular Biochem. (Keystone Symposia on Molecular and Cellular Biology, 18–25 Jan.), Suppl. 15B, p. 26, abstract CA 211.

*Hackh's Chemical Dictionary*, Grant et al. (ed.) McGraw-Hill Book Company, New York, p. 312.

Farese et al., "Antisense DNA downregulates protein kinase C isozymes (beta and alpha) and insulin-stimulated 2-deoxyglucose uptake in rat adipocytes," *Antisense Res. Dev.*, (1):35–42 (1991).

Maier et al., "An oligomer targeted against protein kinase C alpha prevents interleukin-1 alpha induction of cyclooxygenase expression in human endothelial cells," *Exp. Cell Res.*, 205 (1): 52–58 (1993).

Baxter et al., "PKC-episilon is involved in granulocyte-macrophage colony-stimulating factor signal transduction: Evidence from microphysiometry and antisense oligonucleotide experiments," *Biochemistry*, 31: 10950–10954 (1992).

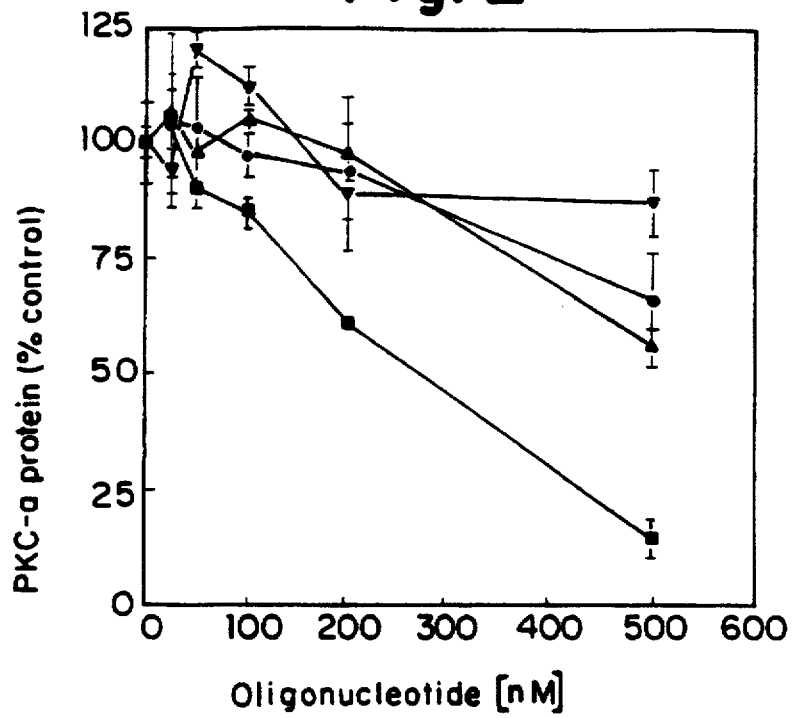
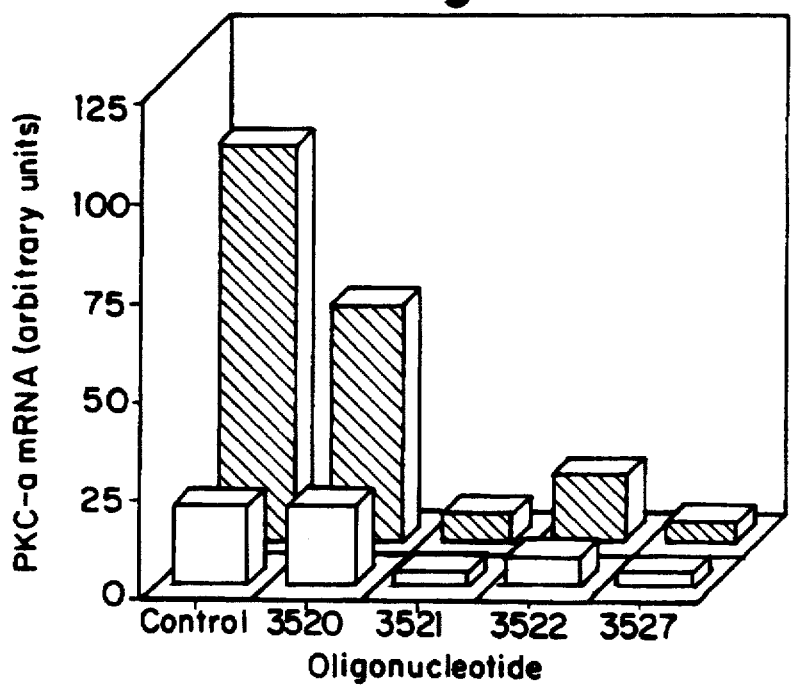

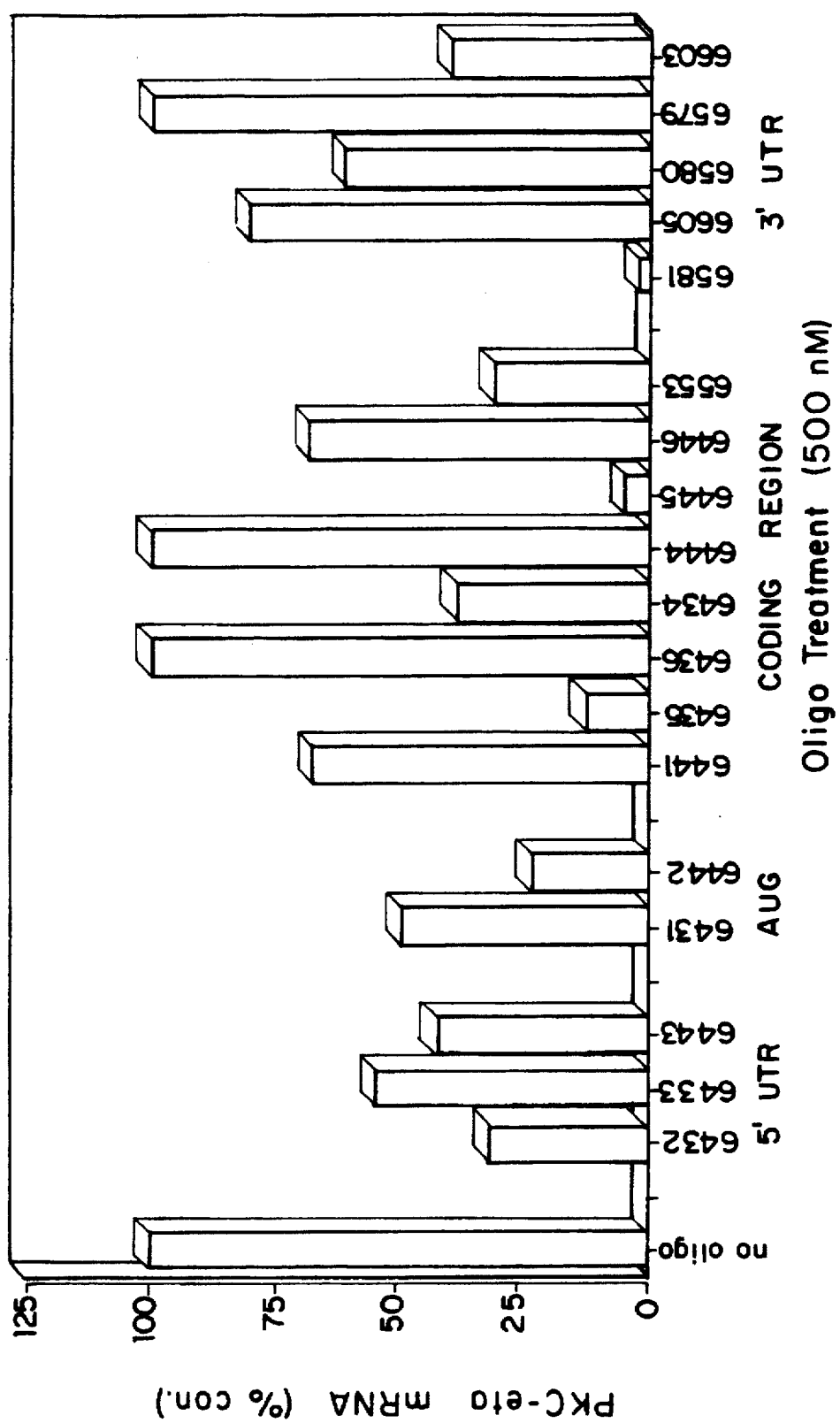

SEQUENCE LISTING ( 1 ) GENERAL INFORMATION:

( i i i ) NUMBER OF SEQUENCES: 62

( 2 ) INFORMATION FOR SEQ ID NO: 1:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 1:

CCCCAACCAC CTCTTGCTCC        2 0

( 2 ) INFORMATION FOR SEQ ID NO: 2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 2:

GTTCTCGCTG GTGAGTTTCA 20

( 2 ) INFORMATION FOR SEQ ID NO: 3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 3:

AAAACGTCAG CCATGGTCCC 20

( 2 ) INFORMATION FOR SEQ ID NO: 4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 4:

GGATTCACTT CCACTGCGGG 20

( 2 ) INFORMATION FOR SEQ ID NO: 5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 5:

GAGACCCTGA ACAGTTGATC 20

( 2 ) INFORMATION FOR SEQ ID NO: 6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 6:

CCCGGGAAAA CGTCAGCCAT 20

( 2 ) INFORMATION FOR SEQ ID NO: 7:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 7:

CTGCCTCAGC GCCCCTTTGC 20

( 2 ) INFORMATION FOR SEQ ID NO: 8:

-continued ( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 8:

AGTCGGTGCA GTGGCTGGAG 20

( 2 ) INFORMATION FOR SEQ ID NO: 9:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 9:

GCAGAGGCTG GGGACATTGA 20

( 2 ) INFORMATION FOR SEQ ID NO: 10:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 10:

GGGCTGGGGA GGTGTTTGTT 20

( 2 ) INFORMATION FOR SEQ ID NO: 11:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 11:

CACTGCGGGG AGGGCTGGGG 20

( 2 ) INFORMATION FOR SEQ ID NO: 12:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 12:

AGCCGTGGCC TTAAAATTTT 20

( 2 ) INFORMATION FOR SEQ ID NO: 13:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 13:

ATTTTCAGGC CTCCATATGG        20

( 2 ) INFORMATION FOR SEQ ID NO: 14:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 14:

AAGAGAGAGA CCCTGAACAG        20

( 2 ) INFORMATION FOR SEQ ID NO: 15:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 15:

GATAATGTTC TTGGTTGTAA        20

( 2 ) INFORMATION FOR SEQ ID NO: 16:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 16:

ATGGGGTGCA CAAACTGGGG        20

( 2 ) INFORMATION FOR SEQ ID NO: 17:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 17:

GTCAGCCATG GTCCCCCCCC        20

( 2 ) INFORMATION FOR SEQ ID NO: 18:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 18:

-continued

CGCCGTGGAG TCGTTGCCCG 20

( 2 ) INFORMATION FOR SEQ ID NO: 19:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 19:

TCAAATGGAG GCTGCCCGGC 20

( 2 ) INFORMATION FOR SEQ ID NO: 20:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 20:

TGGAATCAGA CACAAGCCGT 20

( 2 ) INFORMATION FOR SEQ ID NO: 21:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 21:

CATCTTGCGC GCGGGGAGCC 20

( 2 ) INFORMATION FOR SEQ ID NO: 22:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 22:

TGCGCGCGGG GAGCCGGAGC 20

( 2 ) INFORMATION FOR SEQ ID NO: 23:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 23:

CGAGAGGTGC CGGCCCCGGG 20

( 2 ) INFORMATION FOR SEQ ID NO: 24:

( i ) SEQUENCE CHARACTERISTICS:
  ( A ) LENGTH: 20
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 24:

CTCTCCTCGC CCTCCGTCGG 20

( 2 ) INFORMATION FOR SEQ ID NO: 25:

( i ) SEQUENCE CHARACTERISTICS:
  ( A ) LENGTH: 20
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 25:

TGGAGTTTGC ATTCACCTAC 20

( 2 ) INFORMATION FOR SEQ ID NO: 26:

( i ) SEQUENCE CHARACTERISTICS:
  ( A ) LENGTH: 20
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 26:

AAAGGCCTCT AAGACAAGCT 20

( 2 ) INFORMATION FOR SEQ ID NO: 27:

( i ) SEQUENCE CHARACTERISTICS:
  ( A ) LENGTH: 20
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 27:

GCCAGCATGT GCACCGTGAA 20

( 2 ) INFORMATION FOR SEQ ID NO: 28:

( i ) SEQUENCE CHARACTERISTICS:
  ( A ) LENGTH: 20
  ( B ) TYPE: nucleic acid
  ( C ) STRANDEDNESS: single
  ( D ) TOPOLOGY: linear ( i v ) ANTI-SENSE: yes ( x i ) SEQUENCE DESCRIPTION: SEQ ID NO: 28:

ACACCCCAGG CTCAACGATG 20

( 2 ) INFORMATION FOR SEQ ID NO: 29:

( i ) SEQUENCE CHARACTERISTICS:
  ( A ) LENGTH: 20
  ( B ) TYPE: nucleic acid
  ( C ) STRANDEDNESS: single
  ( D ) TOPOLOGY: linear (i v) ANTI-SENSE: yes (x i) SEQUENCE DESCRIPTION: SEQ ID NO: 29:

CCGAAGCTTA CTCACAATTT 20

(2) INFORMATION FOR SEQ ID NO: 30:

(i) SEQUENCE CHARACTERISTICS:
    (A) LENGTH: 20
    (B) TYPE: nucleic acid
    (C) STRANDEDNESS: single
    (D) TOPOLOGY: linear (i v) ANTI-SENSE: yes (x i) SEQUENCE DESCRIPTION: SEQ ID NO: 30:

ACTTAGCTCT TGACTTCGGG 20

(2) INFORMATION FOR SEQ ID NO: 31:

(i) SEQUENCE CHARACTERISTICS:
    (A) LENGTH: 20
    (B) TYPE: nucleic acid
    (C) STRANDEDNESS: single
    (D) TOPOLOGY: linear (i v) ANTI-SENSE: yes (x i) SEQUENCE DESCRIPTION: SEQ ID NO: 31:

ATGCTGCGGA AAATAAATTG 20

(2) INFORMATION FOR SEQ ID NO: 32:

(i) SEQUENCE CHARACTERISTICS:
    (A) LENGTH: 20
    (B) TYPE: nucleic acid
    (C) STRANDEDNESS: single
    (D) TOPOLOGY: linear (i v) ANTI-SENSE: yes (x i) SEQUENCE DESCRIPTION: SEQ ID NO: 32:

ATTTTATTTT GAGCATGTTC 20

(2) INFORMATION FOR SEQ ID NO: 33:

(i) SEQUENCE CHARACTERISTICS:
    (A) LENGTH: 20
    (B) TYPE: nucleic acid
    (C) STRANDEDNESS: single
    (D) TOPOLOGY: linear (i v) ANTI-SENSE: yes (x i) SEQUENCE DESCRIPTION: SEQ ID NO: 33:

TTTGGGGATG AGGGTGAGCA 20

(2) INFORMATION FOR SEQ ID NO: 34:

(i) SEQUENCE CHARACTERISTICS:
    (A) LENGTH: 20
    (B) TYPE: nucleic acid
    (C) STRANDEDNESS: single
    (D) TOPOLOGY: linear (i v) ANTI-SENSE: yes (x i) SEQUENCE DESCRIPTION: SEQ ID NO: 34:

CCCATTCCCA CAGGCCTGAG 20

( 2 ) INFORMATION FOR SEQ ID NO: 35:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 35:

CGGAGCGCGC CAGGCAGGGA 20

( 2 ) INFORMATION FOR SEQ ID NO: 36:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 36:

CCTTTTCCCA GACCAGCCAT 20

( 2 ) INFORMATION FOR SEQ ID NO: 37:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 37:

GGCCCCAGAA ACGTAGCAGG 20

( 2 ) INFORMATION FOR SEQ ID NO: 38:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 38:

GGATCCTGCC TTTCTTGGGG 20

( 2 ) INFORMATION FOR SEQ ID NO: 39:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 39:

CAGCCATGGC CCCAGAAACG 20

( 2 ) INFORMATION FOR SEQ ID NO: 40:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 40:

CGACATGCCG GCGCCGCTGC 20

( 2 ) INFORMATION FOR SEQ ID NO: 41:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 41:

CAGACGACAT GCCGGCGCCG 20

( 2 ) INFORMATION FOR SEQ ID NO: 42:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 42:

GCCTGCTTCG CAGCGGGAGA 20

( 2 ) INFORMATION FOR SEQ ID NO: 43:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 43:

ACAGGTGCAG GAGTCGAGGC 20

( 2 ) INFORMATION FOR SEQ ID NO: 44:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 44:

GTCCCGTCTC AGGCCAGCCC 20

( 2 ) INFORMATION FOR SEQ ID NO: 45:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear (i v) ANTI-SENSE: yes (x i) SEQUENCE DESCRIPTION: SEQ ID NO: 45:

CCTCACCGAT GCGGACCCTC 20

(2) INFORMATION FOR SEQ ID NO: 46:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 46:

ATTGAACTTC ATGGTGCCAG 20

(2) INFORMATION FOR SEQ ID NO: 47:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 47:

TCTCACTCCC CATAAGGCTA 20

(2) INFORMATION FOR SEQ ID NO: 48:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 48:

TTCCTTTGGG TTCTCGTGCC 20

(2) INFORMATION FOR SEQ ID NO: 49:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 49:

TTCCATCCTT CGACAGAGTT 20

(2) INFORMATION FOR SEQ ID NO: 50:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 50:

AGGCTGATGC TGGGAAGGTC  20

( 2 ) INFORMATION FOR SEQ ID NO: 51:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 51:

GTTCTAAGGC TGATGCTGGG  20

( 2 ) INFORMATION FOR SEQ ID NO: 52:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO:52:

TTCTCGCTGG TGAGTTTC      18

( 2 ) INFORMATION FOR SEQ ID NO: 53:

( i ) SEQUENCE CHARACTERISTICS:
    ( A ) LENGTH: 17
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 53:

TCTCGCTGGT GAGTTTC    17

( 2 ) INFORMATION FOR SEQ ID NO: 54:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 54:

AACTCGAGGT GGCCGCCGTC  20

( 2 ) INFORMATION FOR SEQ ID NO: 55:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 55:

CGCCTTCGCA TAGCCCTTTG  20

( 2 ) INFORMATION FOR SEQ ID NO: 56:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 56:

GGAAGGGGTG ATTGCGGGCC         20

( 2 ) INFORMATION FOR SEQ ID NO: 57:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 57:

AACACGCCCA TTGCCCACCA         20

( 2 ) INFORMATION FOR SEQ ID NO: 58:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 58:

GTCTCAAGAT GGCGTGCTCG         20

( 2 ) INFORMATION FOR SEQ ID NO: 59:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 59:

GCGATGGTTC AGCTGGGCCC         20

( 2 ) INFORMATION FOR SEQ ID NO: 60:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 60:

GCCCTCTCTC TCACTCCCCA         20

( 2 ) INFORMATION FOR SEQ ID NO: 61:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear (iv) ANTI-SENSE: yes (xi) SEQUENCE DESCRIPTION: SEQ ID NO: 61:

CTGGGAAGGT CCGATAGAGG        20

(2) INFORMATION FOR SEQ ID NO: 62:

(i) SEQUENCE CHARACTERISTICS:
    (A) LENGTH: 20
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 62:

AAGGCTGATG CTGGGAAGGT        20

OLIGONUCLEOTIDE MODULATION OF PROTEIN KINASE C

This application is a continuation in part of Ser. No. 852,852 filed Mar. 16, 1992 now abandoned.

FIELD OF THE INVENTION

This invention relates to therapies, diagnostics, and research reagents for disease states which respond to modulation of the expression of protein kinase C. In particular, this invention relates to antisense oligonucleotides specifically hybridizable with nucleic acids relating to protein kinase C. These oligonucleotides have been found to modulate the expression of protein kinase C. Palliation and therapeutic effect result.

BACKGROUND OF THE INVENTION

The phosphorylation of proteins plays a key role in the transduction of extracellular signals into the cell. The enzymes, called kinases, which effect such phosphorylations are targets for the action of growth factors, hormones, and other agents involved in cellular metabolism, proliferation and differentiation. One of the major signal transduction pathways involves the enzyme protein kinase C (PKC), which is known to have a critical influence on cell proliferation and differentiation. PKC is activated by diacylglycerols (DAGs), which are metabolites released in signal transduction.

Interest in PKC was stimulated by the finding that PKC is the major, and perhaps only, cellular receptor through which a class of tumor-promoting agents called phorbol esters exert their pleiotropic effects on cells [Gescher et al., *Anti-Cancer Drug Design* 4:93–105 (1989)]. Phorbols capable of tumor production can mimic the effect of DAG in activating PKC, suggesting that these tumor promoters act through PKC and that activation of this enzyme is at least partially responsible for the resulting tumorigenesis [Parker et al., *Science* 233:853–866 (1986)].

Experimental evidence indicates that PKC plays a role in growth control in colon cancer. It is believed that specific bacteria in the intestinal tract convert lipids to DAG, thus activating PKC and altering cell proliferation. This may explain the correlation between high dietary fat and colon cancer [Weinstein, *Cancer Res. (Suppl.)* 51:5080s–5085s (1991)]. It has also been demonstrated that a greater proportion of the PKC in the colonic mucosa of patients with colorectal cancer is in an activated state compared to that of patients without cancer [Sakanoue et al., *Int. J. Cancer* 48:803–806 (1991)].

Increased tumorigenicity is also correlated with overexpression of PKC in cultured cells inoculated into nude mice. A mutant form of PKC induces highly malignant tumor cells with increased metastatic potential. Sphingosine and related inhibitors of PKC activity have been shown to inhibit tumor cell growth and radiation-induced transformation in vivo [Endo et al., *Cancer Research* 51:1613–1618 (1991); Borek et al., *Proc. Natl. Acad. Sci.* 88:1953–1957 (1991)]. A number of experimental or clinically useful anti-cancer drugs show modulatory effects on PKC. Therefore, inhibitors of PKC may be important cancer-preventive or therapeutic agents. PKC has been suggested as a plausible target for more rational design of conventional anti-cancer drugs [Gescher, A. and Dale, I. L., *Anti-Cancer Drug Design*, 4:93–105 (1989)].

Experiments also indicate that PKC plays an important role in the pathophysiology of hyperproliferative skin disorders such as psoriasis and skin cancer. Psoriasis is characterized by inflammation, hyperproliferation of the epidermis and decreased differentiation of cells. Various studies indicate a role for PKC in causing these symptoms. PKC stimulation in cultured keratinocytes can be shown to cause hyperproliferation. Inflammation can be induced by phorbol esters and is regulated by PKC. DAG is implicated in the involvement of PKC in dermatological diseases, and is formed to an increased extent in psoriatic lesions.

Inhibitors of PKC have been shown to have both antiproliferative and antiinflammatory effects in vitro. Some antipsoriasis drugs, such as cyclosporine A and anthralin, have been shown to inhibit PKC. Inhibition of PKC has been suggested as a therapeutic approach to the treatment of psoriasis [Hegemann, L. and G. Mahrle, *Pharmacology of the Skin*, H. Mukhtar, ed., p. 357–368, CRC Press, Boca Raton, Fla., 1992].

PKC is not a single enzyme, but a family of enzymes. At the present time at least seven isoforms (isozymes) of PKC have been identified: isoforms $\alpha$, $\beta$, and $\gamma$ have been purified to homogeneity, and isoforms $\delta$, $\epsilon$, $\zeta$ and $\eta$ have been identified by molecular cloning. These isozymes have distinct patterns of tissue and organ localization (see Nishizuka, *Nature*, 334:661–665 (1988) for review) and may serve different physiological functions. For example, PKC-$\gamma$ seems to be expressed only in the central nervous system. PKC-$\alpha$ and -$\beta$ are expressed in most tissues, but have different patterns of expression in different cell types. For example, both PKC-$\alpha$ and PKC-$\beta$ are expressed in, and have been purified from, human epidermis. While PKC-$\alpha$ has been detected mainly in keratinocytes of the basal layers of the epidermis, PKC-$\beta$ is found mainly in the middle layers of the epidermis and Langerhans cells. PKC-$\eta$ has been found predominantly in the skin and lungs, with levels of expression much higher in these tissues than in the brain. This is in contrast to other members of the PKC family which tend to be most abundantly expressed in the brain [Osada et al., *J. Biol. Chem.* 265:22434–22440 (1990)]. While the PKC isozymes listed here are preferred for targeting by the present invention, other isozymes of PKC are also comprehended by the present invention.

It is presently believed that different PKC isozymes may be involved in various disease processes depending on the organ or tissue in which they are expressed. For example, in psoriatic lesions there is an alteration in the ratio between PKC-$\alpha$ and PKC-$\beta$, with preferential loss of PKC-$\beta$ compared to normal skin [Hegemann, L. and G. Mahrle, *Pharmacology of the Skin*, H. Mukhtar, ed., p. 357–368, CRC Press, Boca Raton, Fla., 1992].

Although numerous compounds have been identified as PKC inhibitors (see Hidaka and Hagiwara, *Trends in Pharm. Sci.* 8:162–164 (1987) for review), few have been found which inhibit PKC specifically. While the quinoline sulfonamide derivatives such as 1-(5-isoquinolinesulfonyl)-2-methylpiperazine (H-7) inhibit PKC at micromolar concentrations, they exhibit similar enzyme inhibition kinetics for PKC and the cAMP-dependent and cGMP-dependent protein kinases. Staurosporine, an alkaloid product of Streptomyces sp., and its analogs, are the most potent in vitro inhibitors of PKC identified to date. However, they exhibit only limited selectivity among different protein kinases [Gescher, *Anti-Cancer Drug Design* 4:93–105 (1989)]. Certain ceramides and sphingosine derivatives have been shown to have PKC inhibitory activity and to have promise for therapeutic uses, however, there remains a long-felt need for specific inhibitors of the enzymes.

There is also a desire to inhibit specific PKC isozymes, both as a research tool and as treatment for diseases which may be associated with particular isozymes. Godson et al. [*J. Biol. Chem.* 268:11946–11950 (1993)] recently disclosed use of stable transfection of antisense PKC-α cDNA in cytomegalovirus promotor-based expression vectors to specifically decrease expression of PKC-α protein by approximately 70%. It was demonstrated that this inhibition causes a loss of phospholipase $A_2$-mediated arachidonic acid release in response to the phorbol ester PMA. Attempts by the same researchers at inhibiting PKC activity with oligodeoxynucleotides were ultimately unsuccessful due to degradation of oligonucleotides.

OBJECTS OF THE INVENTION

It is a principal object of the invention to provide therapies for neoplastic, hyperproliferative, inflammatory and other disease states associated with protein kinase C.

Another object of the invention is to provide selective therapies for diseases associated with particular isozymes of protein kinase C.

It is a further object of the invention to provide antisense oligonucleotides which are capable of modulating the expression of protein kinase C.

Another object of the invention is to provide antisense oligonucleotides which are capable of selectively modulating the expression of particular isozymes of protein kinase C.

Yet another object is to provide means for diagnosis of diseases associated with protein kinase C.

A further object of the invention is to provide means for differential diagnosis of diseases associated with particular isozymes of protein kinase C.

A still further object of the invention is to provide research tools for the study of the effects of protein kinase C expression and diseases associated therewith.

An additional object of the invention is to provide research tools for the study of the effects of expression of particular isozymes of protein kinase C and diseases associated therewith.

These and other objects of this invention will become apparent from a review of the instant specification.

BRIEF DESCRIPTION OF THE DRAWINGS

FIG. 2 is a line graph showing dose-dependent reduction of PKC-α protein levels after oligonucleotide treatment of A549 cells. ▼=ISIS 4632; ■=ISIS 4649; •=ISIS 4636; ▲=ISIS 4648.

FIG. 3 is a bar graph showing reduction of PKC-α mRNA after treatment of A549 cells with oligonucleotides. Hatched bars represent the 8.5 kb transcript, plain bars represent the 4.0 kb transcript.

FIG. 9 is a set of bar graphs showing the effect of additional oligonucleotides on PKC-α mRNA levels.

FIG. 11 is a set of line graphs showing effect of oligonucleotides on growth of human MDA-MB231 tumors in nude mice.

FIG. 12 is a bar graph showing effect of 20-mer phosphorothioate oligonucleotides on PKC-η expression in A549 cells.

SUMMARY OF THE INVENTION

Figure 1A:
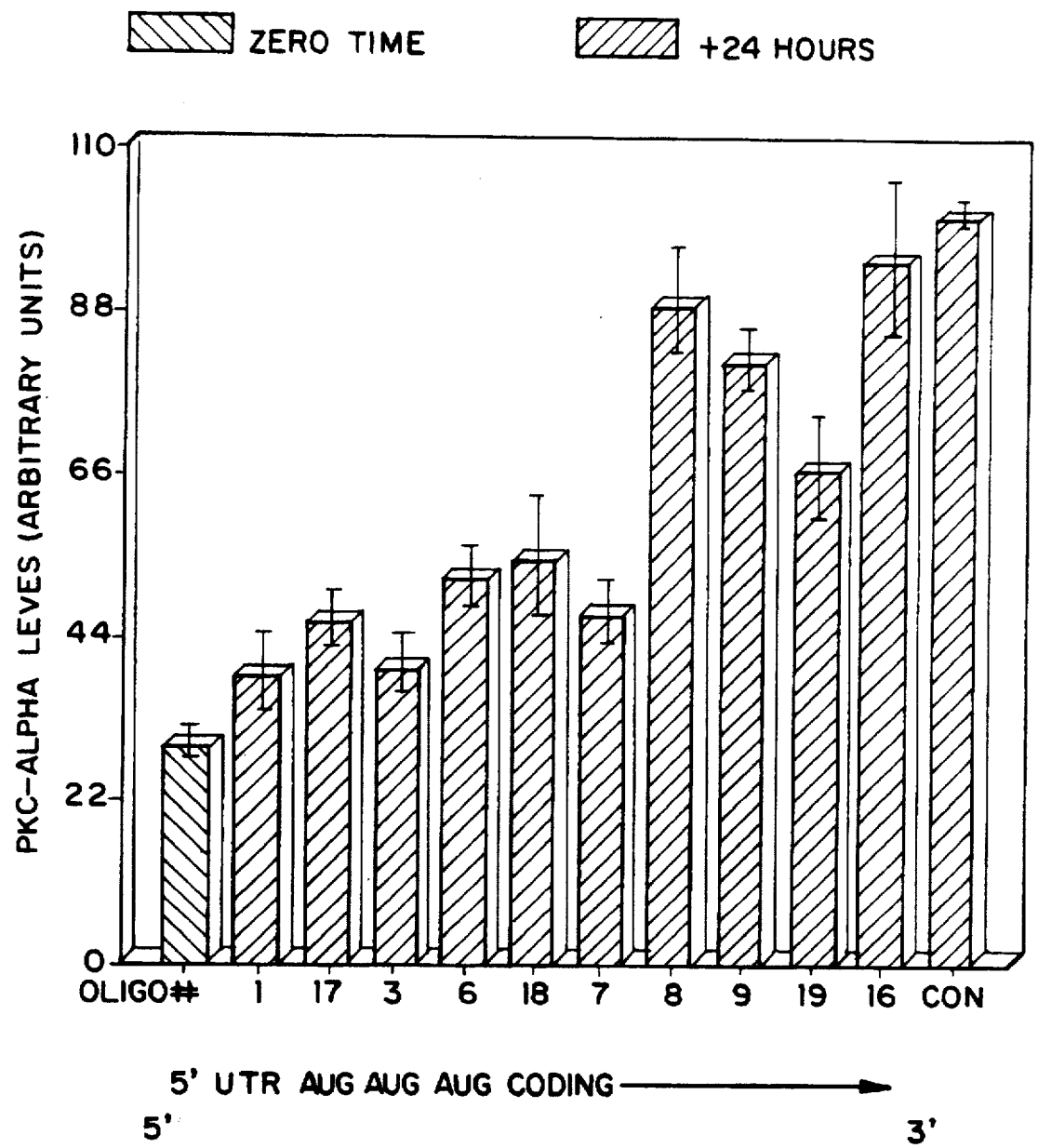
FIGS. 1(a) and 1(b) are graphical depictions of the effects on PKC expression of antisense oligonucleotides hybridizable with PKC-α. Oligonucleotides are arranged by PKC target region, 5' to 3'.

In accordance with the present invention, oligonucleotides are provided that are specifically hybridizable with DNA or RNA deriving from the gene that encodes PKC. The oligonucleotide comprises nucleotide units sufficient in identity and number to effect such specific hybridization. This relationship is commonly denominated as "antisense". In one preferred embodiment, the oligonucleotides are specifically hybridizable with the translation initiation codon of the gene, and preferably comprise a sequence CAT. In another preferred embodiment, the oligonucleotides are specifically hybridizable with the 5'-untranslated or 3'-untranslated regions of the gene. In yet another preferred embodiment, oligonucleotides are provided that are specifically hybridizable with DNA or mRNA encoding a particular PKC isozyme or a particular set of PKC isozymes. Such oligonucleotides may be conveniently and desirably presented in a pharmaceutically acceptable carrier.

In accordance with other preferred embodiments, the oligonucleotides comprise one or more chemical modifications which convey some desired characteristic such as improved target affinity, cellular uptake or stability in the presence of cellular nucleases. Examples of modifications having such utility are 2'-O-alkyl and 2'-fluoro sugar modifications and phosphorothioate backbone modifications.

Other aspects of the invention are directed to methods for modulating the expression of PKC or of a particular PKC isozyme or set of isozymes in cells or tissues. Additional aspects of the invention are directed to methods of detection in cells or tissues of the DNA or RNA that encodes PKC and specific detection in cells or tissues of RNA or DNA that encodes particular PKC isozymes. Such methods comprise contacting cells or tissues suspected of containing said gene with oligonucleotides in accordance with the invention in order to interfere with the effect of or to detect said RNA or DNA.

Other aspects of the invention are directed to methods for diagnostics and therapeutics of animals suspected of having a disease associated with PKC or one of its isozymes. Such methods comprise contacting the animal or cells or tissues or a bodily fluid from the animal with oligonucleotides in accordance with the invention in order to modulate the expression of PKC, to treat conditions associated with PKC, or to effect a diagnosis thereof.

DETAILED DESCRIPTION OF THE INVENTION

Antisense oligonucleotides are now accepted as therapeutic agents having promise for the treatment of many human diseases. Oligonucleotides specifically bind (hybridize) to the complementary sequence of DNA, pre-mRNA or mature mRNA, as defined by Watson-Crick base pairing, interfering with the flow of genetic information from DNA to protein. The properties of antisense oligonucleotides which make them specific for their target sequence also make them extraordinarily versatile. Because antisense oligonucleotides are long chains of monomeric units, they may be readily synthesized for any target RNA sequence. Numerous recent studies have documented the utility of antisense oligonucleotides as biochemical tools for studying target proteins (Rothenberg et al., *J. Natl. Cancer Inst.*, 81:1539–1544 (1989); Zon, G., *Pharmaceutical Res.*, 5:539–549 (1988). Because of recent advances in oligonucleotide chemistry and synthesis of oligonucleotides which exhibit enhanced cell uptake, target binding affinity and nuclease resistance, it is now possible to consider the use of antisense oligonucleotides as a novel form of therapeutics. For example, antisense oligonucleotides targeted to c-myb have been used to completely eliminate myeloid leukemia cells from bone marrow derived from patients with acute myelogenous leukemia. Gewirtz and Calabretta, U.S. Pat. No. 5,098,890.

Antisense oligonucleotides offer an ideal solution to the problems encountered in prior art approaches. They can be designed to selectively inhibit a given isozyme or particular set of isozymes, or to inhibit all members of a given family of isozymes. They avoid non-specific mechanisms such as free radical scavenging. A complete understanding of enzyme mechanism is not needed to design specific inhibitors.

Current agents which modulate the activity or metabolism of protein kinase C exhibit many unacceptable side effects due to their lack of specificity, or they exhibit only limited effectiveness in inhibiting the enzyme. The instant invention circumvents problems encountered by prior workers by modulating the production of the enzyme, rather than inhibiting the enzyme directly, to achieve the therapeutic effect. In the instant invention, the oligonucleotide is designed to bind directly to mRNA or to a gene, ultimately modulating the amount of PKC protein made from the gene.

In the context of this invention, the term "oligonucleotide" refers to a polynucleotide formed from naturally occurring nucleobases and pentofuranosyl (sugar) groups joined by native phosphodiester bonds. This term effectively refers to naturally occurring species or synthetic species formed from naturally occurring subunits or their close homologs.

The term "oligonucleotide" may also refer to moieties which function similarly to naturally occurring oligonucleotides but which have non-naturally occurring portions. Thus, oligonucleotides may have altered sugar moieties, nucleobases or inter-sugar ("backbone") linkages. Such modified or substituted oligonucleotides are often preferred over native forms because of properties such as, for example, enhanced cellular uptake, enhanced target binding affinity and increased stability in the presence of nucleases.

Specific examples of some preferred oligonucleotides envisioned for this invention are those which contain intersugar backbone linkages such as phosphotriesters, methyl phosphonates, short chain alkyl or cycloalkyl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—P—O—$CH_2$). Phosphorothioates are also most preferred. Also preferred are oligonucleotides having morpholino backbone structures. Summerton, J. E. and Weller, D. D., U.S. Pat. No. 5,034,506. In other preferred embodiments, such as the peptide nucleic acid (PNA—referred to by some as "protein nucleic acid") backbone, the phosphodiester backbone of the oligonucleotide may be replaced with a polyamide backbone wherein nucleosidic bases are bound directly or indirectly to aza nitrogen atoms or methylene groups in the polyamide backbone. see, e.g., P. E. Nielsen, M. Egholm, R. H. Berg, O. Buchardt, *Science* 1991, 254, 1497 and U.S. patent application Ser. No. 08/054,363, filed Apr. 26, 1993 and incorporated herein by reference. In accordance with other preferred embodiments, the phosphodiester bonds are substituted with structures which are chiral and enantiomerically specific. Persons of ordinary skill in the art will be able to select other linkages for use in practice of the invention.

Oligonucleotides may also include species which include at least one modified nucleobase. Thus, purines and pyrimidines other than those normally found in nature may be so employed. Similarly, modifications on the pentofuranosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

Chimeric or "gapped" oligonucleotides are also preferred embodiments of the invention. These oligonucleotides contain two or more chemically distinct regions, each comprising at least one nucleotide. Typically, one or more region comprises modified nucleotides that confer one or more beneficial properties, for example, increased nuclease resistance, increased uptake into cells or increased binding affinity for the RNA target. One or more unmodified or differently modified regions retains the ability to direct Rnase H cleavage. Chimeric oligonucleotides are disclosed in PCT application US92/11339 which is assigned to the assignee of the instant application and which is incorporated by reference herein in its entirety. Examples of chimetic oligonucleotides which are presently preferred are 2'-O- methyl or 2'-O-propyl oligonucleotides having a "deoxy gap" region of 2'-deoxynucleotides. Usually this deoxy gap region is located between the two 2'-alkyl regions. In these preferred embodiments, the internucleotide (backbone) linkages may be uniformly phosphorothioate or some combination of phosphorothioate and phosphodiester linkages.

All such oligonucleotides are best described as being functionally interchangeable with natural oligonucleotides (or synthesized oligonucleotides along natural lines), but having one or more differences from natural structure. All such oligonucleotides are comprehended by this invention so long as they function effectively to hybridize with the PKC RNA.

The oligonucleotides in accordance with this invention preferably comprise from about 5 to about 50 nucleotide units. It is more preferred that such oligonucleotides comprise from about 8 to 30 nucleotide units, and still more preferred to have from about 12 to 25 nucleotide units. As will be appreciated, a nucleotide unit is a base-sugar combination (or a combination of analogous structures) suitably bound to an adjacent nucleotide unit through phosphodiester or other bonds forming a backbone structure.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as phosphorothioates or alkylated derivatives. Other modified and substituted oligomers can be similarly synthesized.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, a 5' cap region, an intron/exon junction, coding sequences or sequences in the 5'- or 3'-untranslated region.

The oligonucleotides of this invention are designed to be hybridizable with messenger RNA derived from the PKC gene. Such hybridization, when accomplished, interferes with the normal roles of the messenger RNA to cause a modulation of its function in the cell. The functions of messenger RNA to be interfered with may include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with the RNA function is to modulate expression of the PKC gene.

The oligonucleotides of this invention can be used in diagnostics, therapeutics, prophylaxis, and as research reagents and kits. Since the oligonucleotides of this invention hybridize to the PKC gene and its mRNA, sandwich and other assays can easily be constructed to exploit this fact.

Furthermore, since the oligonucleotides of this invention hybridize specifically to particular isozymes of the PKC mRNA, such assays can be devised for screening of cells and tissues for particular PKC isozymes. Such assays can be utilized for diagnosis of diseases associated with various PKC forms. Provision of means for detecting hybridization of oligonucleotide with the PKC gene can routinely be accomplished. Such provision may include enzyme conjugation, radiolabelling or any other suitable detection systems. Kits for detecting the presence or absence of PKC may also be prepared.

For therapeutic or prophylactic treatment, oligonucleotides are administered in accordance with this invention. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotides.

The pharmaceutical composition may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The following examples illustrate the present invention and are not intended to limit the same.

EXAMPLES

Example 1

Oligonucleotide synthesis:

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized according to the procedures set forth above substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds. Similarly, 2'-O-propyl phosphorothioate oligonucleotides may be prepared by slight modifications of this procedure.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Tris-borate buffer, Ph 7.0.

The oligonucleotides tested are presented in Table 1. Sequence data are from the cDNA sequence published by Finkenzeller et al., Nucl. Acids Res. 18:2183 (1990); Genbank accession number X52479. The sequence numbers given under the oligonucleotides are relative to the first residue to be sequenced on the cDNA, which is 28 residues upstream of the ATG start codon.

TABLE 1

| SEQ ID | OLIGONUCLEOTIDES TARGETED TO HUMAN PKC-α Sequence | Target | ISIS # |
|---|---|---|---|
| 1 | CCC CAA CCA CCT CTT GCT CC<br>19                1 | 5'<br>Untranslated | 3520 |
| 2 | GTT CTC GCT GGT GAG TTT CA<br>2063              2044 | 3'<br>Untranslated | 3521 |
| 3 | AAA ACG TCA GCC ATG GTC CC<br>41                22 | Translation<br>init. codon | 3522 |
| 4 | GGA TTC ACT TCC ACT GCG GG<br>2109              2090 | 3'<br>Untranslated | 3526 |
| 5 | GAG ACC CTG AAC AGT TGA TC<br>2211              2192 | 3'<br>Untranslated | 3527 |
| 6 | CCC GGG AAA ACG TCA GCC AT<br>47                28 | Translation<br>init codon | 3674 |
| 7 | CTG CCT CAG CGC CCC TTT GC<br>110               91 | Internal<br>(C1) domain | 3682 |
| 8 | AGT CGG TGC AGT GGC TGG AG<br>193               174 | Internal<br>(C1) domain | 3686 |
| 9 | GCA GAG GCT GGG GAC ATT GA<br>480               461 | Internal<br>(C1) domain | 3687 |
| 10 | GGG CTG GGG AGG TGT TTG TT<br>2080              2061 | 3'<br>Untranslated | 3695 |
| 11 | CAC TGC GGG GAG GGC TGG GG<br>2098              2079 | 3'<br>Untranslated | 3875 |
| 12 | AGC CGT GGC CTT AAA ATT TT<br>2137              2118 | 3'<br>Untranslated | 3878 |
| 13 | ATT TTC AGG CCT CCA TAT GG<br>2168              2149 | 3'<br>Untranslated | 3879 |
| 14 | AAG AGA GAG ACC CTG AAC AG<br>2217              2198 | 3'<br>Untranslated | 3884 |
| 15 | GAT AAT GTT CTT GGT TGT AA<br>2235              2216 | 3'<br>Untranslated | 3885 |
| 16 | ATG GGG TGC ACA AAC TGG GG<br>2027              2008 | Internal<br>(C3) domain | 3886 |

TABLE 1-continued

| SEQ ID | OLIGONUCLEOTIDES TARGETED TO HUMAN PKC-α Sequence | Target | ISIS # |
|---|---|---|---|
| 17 | GTC AGC CAT GGT CCC CCC CC<br>36                17 | Translation<br>init. codon | 3890 |
| 18 | CGC CGT GGA GTC GTT GCC CG<br>63                44 | Internal<br>(V1) domain | 3891 |
| 19 | TCA AAT GGA GGC TGC CCG GC<br>1643              1624 | Internal<br>(C3) domain | 3892 |
| 20 | TGG AAT CAG ACA CAA GCC GT<br>2151              2132 | 3'<br>Untranslated | 3947 |

Example 2

Cell culture and treatment with phorbol esters and oligonucleotides targeted to PKC-α:

PKC protein half-lives have been reported to vary from 6.7 hours to over 24 hours [Young et al., Biochem. J. 244:775–779 (1987); Ballester et al., J. Biol. Chem. 260:15194–15199 (1985)]. These long half-lives make inhibiting steady-state levels of PKC-α an unwieldy approach when screening antisense oligonucleotides, due to the long incubation times which would be required. We have therefore made use of the ability of phorbol esters to reversibly lower intracellular levels of PKC. Treatment of cells with phorbol esters causes an initial activation of kinase activity, followed by a down-regulation of PKC. For PKC-α this down-regulation has been shown to be a direct consequence of an increased rate of proteolysis of the kinase with no apparent change in synthetic rate.

We determined that in human lung carcinoma (A549) cells, treatment with the phorbol ester 12,13-dibutyrate (PDBu), using a modification of the method of Krug et al., [Krug et al., J. Biol. Chem. 262:11852–11856 (1987)] lowered cellular levels of PKC-α, without affecting PKC-α mRNA levels, and that this effect was reversible. The basis of the assay to screen for potency of oligonucleotides targeting PKC-α is to initially lower PKC-α protein levels by chronic treatment with PDBu, remove PDBu by extensively washing the cells (hence allowing the cells to synthesize fresh PKC-α protein), and incubate the cells with oligonucleotides intended to inhibit the resynthesis of new PKC-α protein.

Procedure: A549 cells (obtained from the American Type Culture Collection, Bethesda Md.) were grown to confluence in 6-well plates (Falcon Labware, Lincoln Park, N.J.) in Dulbecco's modified Eagle's medium (DME) containing 1 g glucose/liter and 10% fetal calf serum (FCS, Irvine Scientific, Santa Ana, Calif.).

Cells were treated with 500 nM PDBu (Sigma Chem. Co., St. Louis, Mo.) for 12–16 hours (overnight). Cells were then washed three times in DME at 37° C., and 1 ml DMA containing 20 μl DOTMA (Lipofectin reagent, BRL, Bethesda, Md.) was added. Oligonucleotides were added to a concentration of 1 μM and the cells were incubated for a further 4 hours at 37° C.

Cells were washed once in 3 ml DME containing 0.1 mg/ml BSA and a further 2 ml DME containing 0.1 mg/ml BSA was added. Oligonucleotides (1 μM) were added and the cells were incubated at 37° C. for 24 hours.

Cells were washed three times in phosphate-buffered saline (PBS) and cellular proteins were extracted in 120 μl sample buffer (60 mM Tris pH 6.8, 2% SDS, 10% glycerol, 10 mM dithiothreitol) and boiled for 5 minutes. Intracellular levels of PKC-α protein were determined by immunoblotting.

Example 3

Immunoblot assay for PKC expression:

Cell extracts were electrophoresed on 10% SDS-PAGE mini-gels. The resolved proteins were transferred to Immobilon-P membrane (Millipore, Bedford Mass.) by electrophoretic transfer and the membrane was blocked for 60 minutes in TBS (Tris-HCl pH 7.4, 150 mM NaCl) containing 5% nonfat milk. The membrane was then incubated for 16 hours at 4° C. with monoclonal antibodies raised against PKC-α (UBI, Lake Placid N.Y.) diluted to 0.2 μg/ml in TBS containing 0.2% nonfat milk. This was followed by three washes in TBS plus 0.2% nonfat milk. The membrane was then incubated for one hour with $^{125}$I-labelled goat antimouse secondary antibody (ICN Radiochemicals, Irvine Calif.). Membranes were then washed extensively in TBS plus 0.2% nonfat milk. Bands were visualized and quantitated using a Phosphorimager (Molecular Dynamics, Sunnyvale, Calif.). PKC-α appears as a single band with a molecular weight of 80 kD.

Figure 1B:
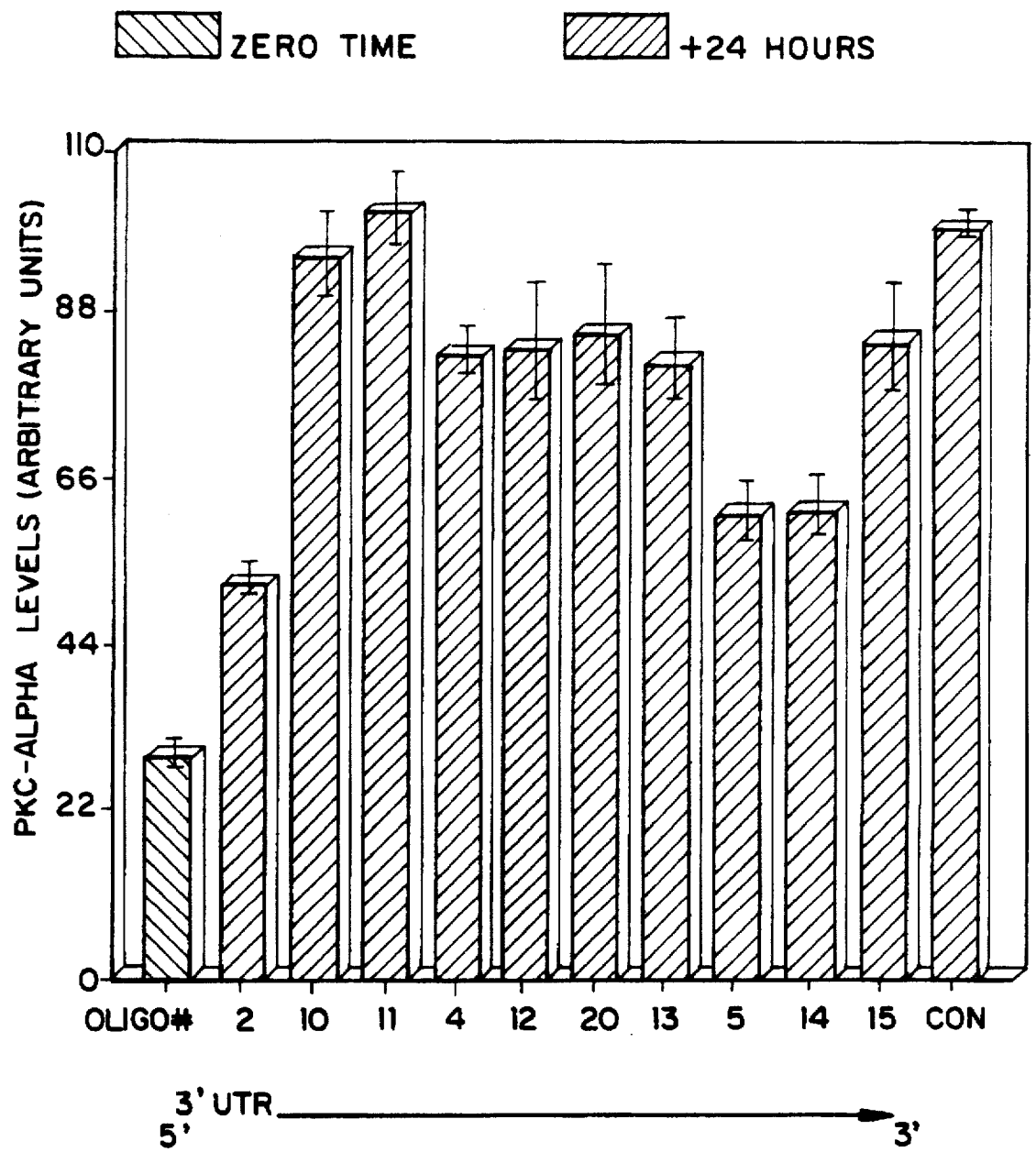

Each oligonucleotide was tested three times, in triplicate, and the results of the experiments were normalized against percentage of protein present as compared to cells which were not treated with oligonucleotide (FIGS. 1a and 1b). The five most effective oligonucleotides target the AUG start codon and regions slightly upstream and downstream from it (Sequence Nos. 1, 3, 17, 7, 6). The next most effective oligonucleotides are targeted toward the 3' untranslated region of the RNA (oligos 2, 5, 14).

Example 4

Other isozymes of PKC:

Results with oligonucleotides targeting human PKC-α demonstrated that the most effective target sequences were those surrounding the translation initiation codon and the 3' untranslated region. It is believed that these sequences will also be effective targets for oligonucleotides directed against other isozymes of PKC. The other isozymes of human PKC for which sequence data are available are PKC-β (types I and II), PKC-γ (partial sequence) and PKC-η. Antisense oligonucleotides which are likely to be effective inhibitors of PKC are identified below. These oligonucleotides are synthesized as in Example 1, and can be screened as in Examples 2 and 3, using appropriate antibodies where available. Alternatively, a reporter gene assay system can be established, transiently co-expressing the desired isozyme of PKC with luciferase under the influence of the TPA-responsive enhancer or other suitable promoter. PKC expression is then assayed by measuring luciferase activity using standard procedures. Luciferase is extracted from cells by lysis with the detergent Triton X-100, as described by Greenberg, M. E., in *Current Protocols in Molecular Biology*, (F. M. Ausubel, R. Brent, R. E. Kingston, D. D. Moore, J. A. Smith, J. G. Seidman and K. Struhl, eds.), John Wiley and Sons, New York (1987). A Dynatech ML1000 luminometer is used to measure peak luminescence upon addition of luciferin (Sigma) to 625 μM.

PKC-β, types I and II

Sequence data are from Kubo et al., *FEBS Lett.* 223: 138–142 (1987); Genbank accession numbers X06318, M27545, X07109. Sequences are numbered from the first 5' base sequenced on the cDNA. PKC-β types I and II are the result of alternative mRNA splicing of a single gene product. This results in proteins with identical amino termini (5' end of the mRNA); however, there is sequence divergence in the carboxy termini (3' end of the mRNA). The following oligonucleotides, targeted to the translation initiation codon, are expected to modulate expression of both PKC-β types I and II:

TABLE 2

OLIGONUCLEOTIDES TARGETED TO PKC-β TYPES I AND II

| SEQ ID | Sequence | Target |
|---|---|---|
| 21 | CAT CTT GCG CGC GGG GAG CC<br>139                                   120 | Translation init. |
| 22 | TGC GCG CGG GGA GCC GGA GC<br>134                                   115 | " |
| 23 | CGA GAG GTG CCG GCC CCG GG<br>113                                   94 | " |
| 24 | CTC TCC TCG CCC TCG CTC GG<br>183                                   164 | " |

The following antisense oligonucleotides are targeted to the 3'-untranslated region of PKC-β type I:

TABLE 3

OLIGONUCLEOTIDES TARGETED TO PKC-β TYPE I

| SEQ. ID | Sequence | Target |
|---|---|---|
| 25 | TGG AGT TTG CAT TCA CCT AC<br>2168                                  2149 | 3' Untranslated |
| 26 | AAA GGC CTC TAA GAC AAG CT<br>2285                                  2266 | " |
| 27 | GCC AGC ATG TGC ACC GTG AA<br>2250                                  2231 | " |
| 28 | ACA CCC CAG GCT CAA CGA TG<br>2186                                  2167 | " |
| 29 | CCG AAG CTT ACT CAC AAT TT<br>2569                                  2550 | " |

The following antisense oligonucleotides are targeted to the 3'-untranslated region of PKC-β Type II:

TABLE 4

OLIGONUCLEOTIDES TARGETED TO PKC-β TYPE II

| SEQ. ID | Sequence | Target |
|---|---|---|
| 30 | ACT TAG CTC TTG ACT TCG GG<br>2160                                  2141 | 3' Untranslated |
| 31 | ATG CTG CGG AAA ATA AAT TG<br>2420                                  2401 | " |
| 32 | ATT TTA TTT TGA GCA TGT TC<br>2663                                  2644 | " |
| 33 | TTT GGG GAT GAG GGT GAG CA<br>2843                                  2824 | " |
| 34 | CCC ATT CCC ACA GGC CTG AG<br>3137                                  3118 | " |

PKC-γ:

Sequence data are from Coussens et al., *Science* 859–866 (1986); Genbank accession number M13977. Sequences are numbered from the first 5' base sequenced in the cDNA. The full sequence is not available: the extreme 3' end of the open reading frame and the 3' untranslated region are missing. Consequently these regions are not presently available as antisense targets.

TABLE 5

OLIGONUCLEOTIDES TARGETED TO PKC-γ

| SEQ. ID | Sequence | Target |
|---|---|---|
| 35 | CGG AGC GCG CCA GGC AGG GA 51                                    32 | 5' Untranslated |
| 36 | CCT TTT CCC AGA CCA GCC AT 215                                    196 | Translation init. |
| 37 | GGC CCC AGA AAC GTA GCA GG 195                                    176 | 5' of start codon |
| 38 | GGA TCC TGC CTT TCT TGG GG 170                                    151 | 5' Untranslated |
| 39 | CAG CCA TGG CCC CAG AAA CG 202                                    183 | Translation init. |

PKC-η:

Sequence data for PKC-η are from Bacher and colleagues [Bacher et al., *Mol. Cell. Biol.* 11:126–133 (1991)]; Genbank accession number M55284. They assign their isozyme the name PKC-L; however the sequence is almost identical to that of mouse PKC-η, so the latter nomenclature is used here for consistency. Sequences are numbered from the first 5' base sequenced in the cDNA.

TABLE 6

OLIGONUCLEOTIDES TARGETED TO PKC-η

| SEQ. ID | Sequence | Target |
|---|---|---|
| 40 | CGA CAT GCC GGC GCC GCT GC 172                                    153 | Translation init. |
| 41 | CAG ACG ACA TGC CGG CGC CG 176                                    157 | " |
| 42 | GCC TGC TTC GCA GCG GGA GA 138                                    119 | " |
| 43 | ACA GGT GCA GGA GTC GAG GC 86                                     67 | " |
| 44 | GTC CCG TGT CAG GCC AGC CC 111                                    92 | " |
| 45 | CCT CAC CGA TGC GGA CCC TC 221                                    202 | " |
| 46 | ATT GAA CTT CAT GGT GCC AG 193                                    174 | " |
| 47 | TCT CAC TCC CCA TAA GGC TA 2946                                   2027 | 3' Untranslated |
| 48 | TTC CTT TGG GTT CTC GTG CC 2067                                   2048 | " |
| 49 | TTC CAT CCT TCG ACA GAG TT 2353                                   2336 | " |
| 50 | AGG CTG ATG CTG GGA AGG TC 2300                                   2281 | " |
| 51 | GTT CTA AGG CTG ATG CTG GG 2306                                   2287 | " |

Example 5

Dose response of phosphorothioate/2'-O-methyl oligonucleotide effects on PKC-α protein synthesis:

A series of phosphorothioate, fully 2'-O-methyl oligonucleotides having SEQ ID NO: 1, 2, 3 and 5 were synthesized. A549 cells were treated with 500 nM PDBu for 18 hours to downregulate PKC-α synthesis, washed to remove PDBu and then treated with oligonucleotide and DOTMA/DOPE cationic liposomes. Medium was replaced after four hours and the cells were allowed to recover for another 20 hours. Proteins were extracted and PKC-α protein levels were determined by immunoblotting as described in Example 3. Results were quantified with a phosphorimager (Molecular Dynamics, Sunnyvale Calif.) and are shown in FIG. 2 expressed as percent of control (saline treatment). ISIS 4649 (SEQ ID NO: 3; squares) reduced PKC-α protein levels by 85–90% at 500 nM and had an IC50 of approximately 260 nM.

Example 6

Effect of antisense oligonucleotides on PKC-α mRNA levels:

A549 cells were treated with phosphorothioate oligonucleotides at 500 nM for four hours in the presence of the cationic lipids DOTMA/DOPE, washed and allowed to recover for an additional 20 hours. Total RNA was extracted and 20 μg of each was resolved on 1.2% gels and transferred to nylon membranes. These blots were probed with a $^{32}$P radiolabeled PKC-α cDNA probe and then stripped and reprobed with a radiolabeled G3PDH probe to confirm equal RNA loading. Each oligonucleotide (3520, 3521, 3522 and 3527) was used in duplicate. The two major PKC-α transcripts (8.5 kb and 4.0 kb) were examined and quantified with a PhosphorImager (Molecular Dynamics, Sunnyvale Calif.). Results are shown in FIG. 3. Oligonucleotides 3521 (SEQ ID NO: 2), 3522 (SEQ ID NO: 3) and 3527 (SEQ ID NO: 5) gave better than 50% reduction of PKC-α mRNA levels. Oligonucleotides 3521 and 3527 gave approximately 80% reduction of the smaller transcript and over 90% reduction of the larger transcript.

Example 7

Figure 4:
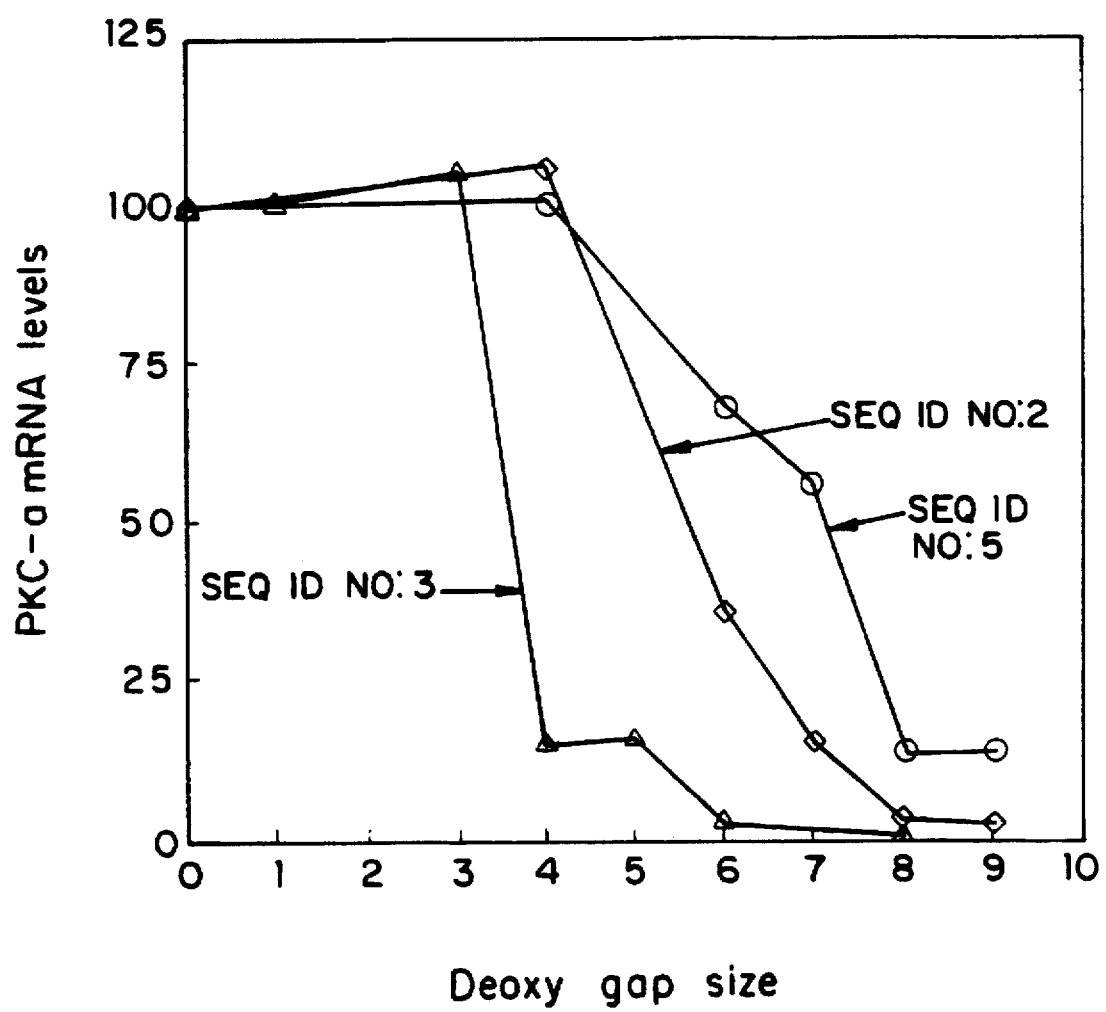
FIG. 4 is a line graph showing the relationship between deoxy gap length and activity of chimeric oligonucleotides against PKC.

Chimeric (deoxy gapped) 2'-O-methyl oligonucleotides:

Oligonucleotides 3521 (SEQ ID NO: 2), 3522 (SEQ ID NO: 3) and 3527 (SEQ ID NO: 5) were chosen for further study and modification. Oligonucleotides having these sequences were synthesized as uniformly phosphorothioate chimeric oligonucleotides having a centered deoxy gap of various lengths flanked by 2'-O-methylated regions. These oligonucleotides (500 nM concentration) were tested for effects on PKC-α mRNA levels by Northern blot analysis. Results are shown in FIG. 4. Deoxy gaps of eight nucleotides or more gave maximal reduction of PKC-α mRNA levels (both transcripts) in all cases. The oligonucleotide having SEQ ID NO: 3 reduced PKC-α mRNA by approximately 83% with a deoxy gap length of four nucleotides, and gave nearly complete reduction of PKC-α mRNA with a deoxy gap length of six or more.

Figure 5:
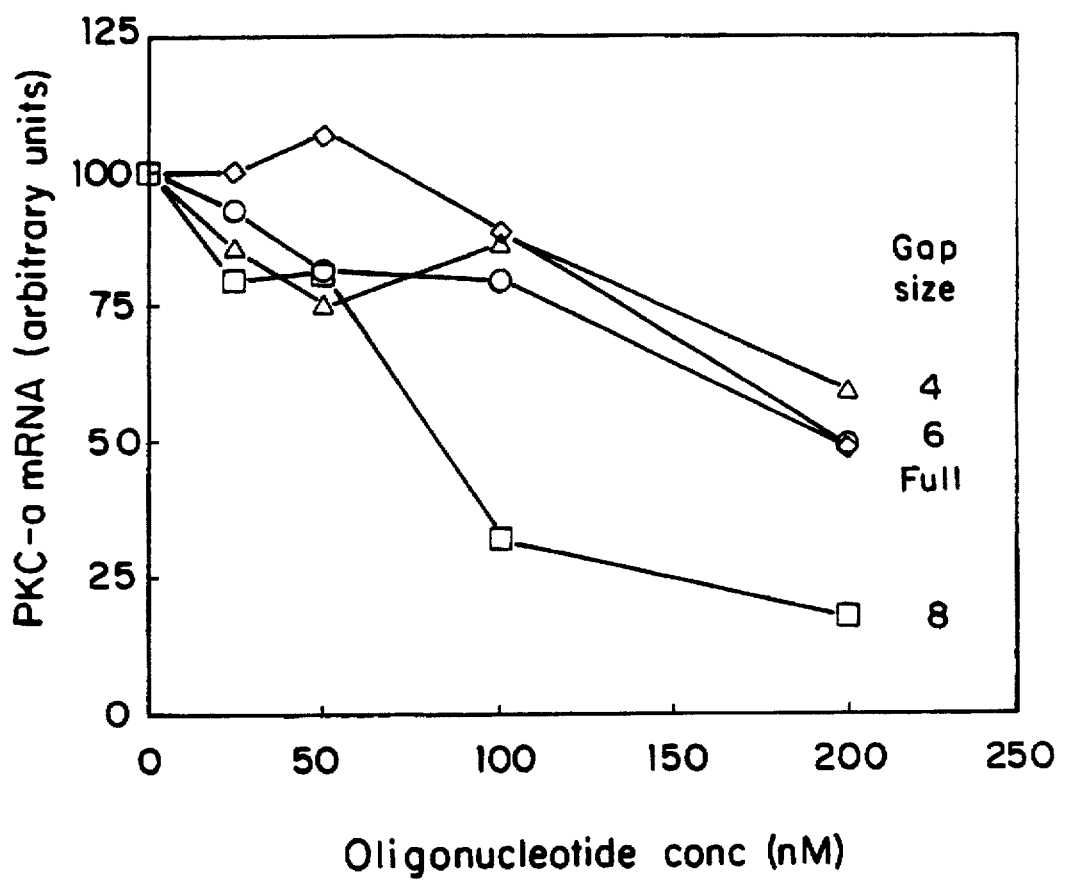
FIG. 5 is a line graph showing dose response curves for chimeric oligonucleotides (all SEQ ID NO: 3) with different deoxy gap lengths.

Dose-response curves for these oligonucleotides are shown in FIG. 5. The 2'-O-methyl chimeric oligonucleotides with four- or six-nucleotide deoxy gaps have an IC50 for PKC-α mRNA reduction (concentration of oligonucleotide needed to give a 50% reduction in PKC-α mRNA levels) of 200–250 nM, as did the full-deoxy oligonucleotide (all are phosphorothioates throughout). The 2'-O-methyl chimeric oligonucleotide with an 8-nucleotide deoxy gap had an IC50 of approximately 85 nM.

Several variations of this chimeric oligonucleotide (SEQ. ID NO: 3) were compared for ability to lower PKC-α mRNA levels. These oligonucleotides are shown in Table 7.

TABLE 7

Chimeric 2'-O-methyl/deoxy P = S oligonucleotides
bold = 2'-O-methyl; s = P = S linkage, o = P = O linkage

| OLIGO # | SEQUENCE | SEQ ID NO: |
|---|---|---|
| 3522 | AsAsAsAsCsGsTsCsAsGsCsCsAsTsGsGsTsCsCsC | 3 |
| 5252 | AsAsAsAsCsGsTsCsAsAsGsCsCsAsTsGsGsTsCsCsC | 3 |
| 6996 | AoAoAoAoCoGsTsCsAsGsCsCsAsTsGoGoToCoCoC | 3 |
| 7008 | AsAoAoAoCoGsTsCsAsGsCsCsAsTsGoGoToCoCsC | 3 |
| 7024 | AsAoAoAoCoGsToCsAoGsCoCsAsTsGoGoToCoCsC | 3 |

Figure 6:
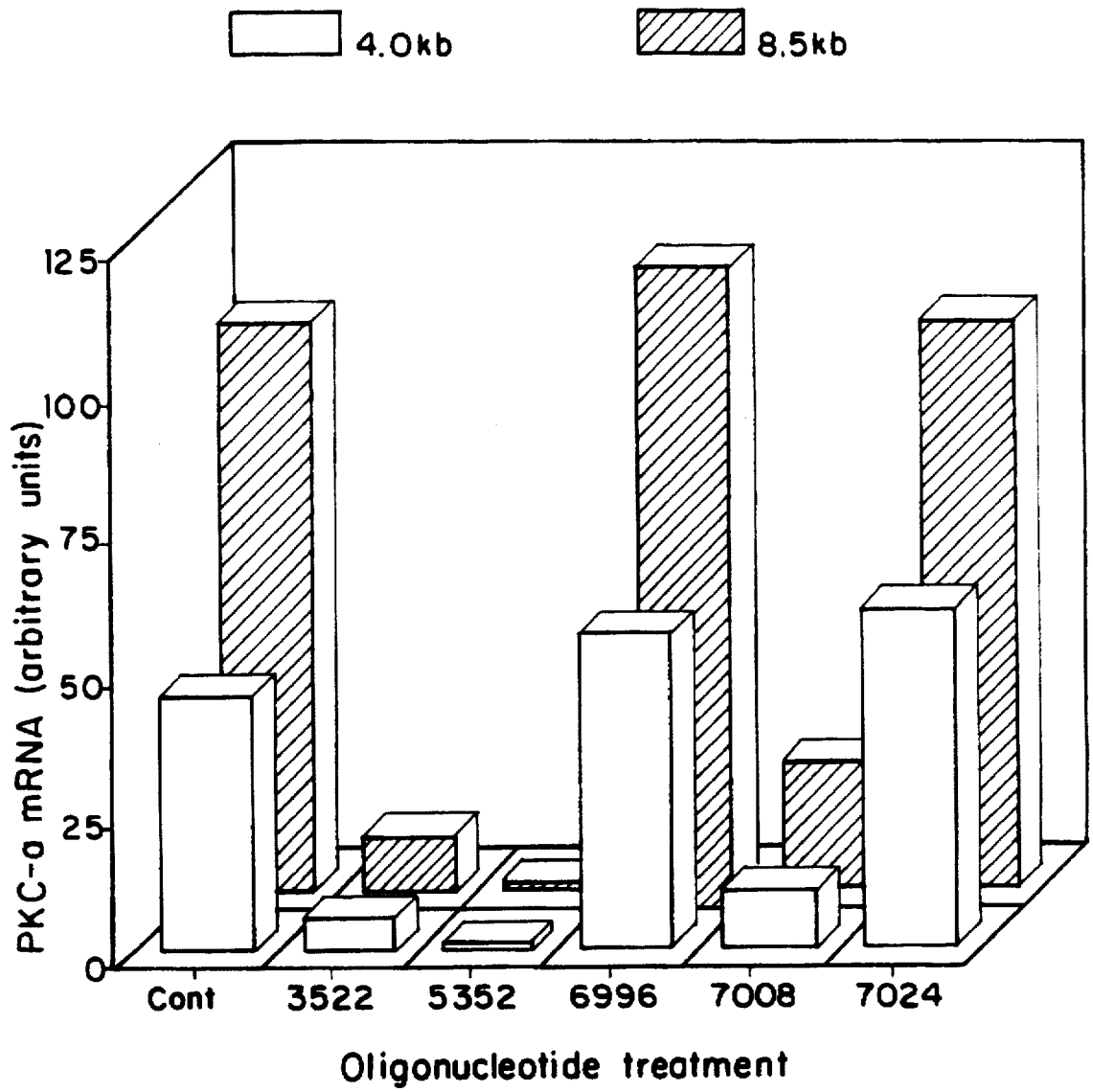
FIG. 6 is a bar graph showing the effects of several 2'-O-methyl chimeric oligonucleotides of SEQ ID NO: 3 on PKC-α mRNA levels. Hatched bars represent the 8.5 kb transcript, plain bars represent the 4.0 kb transcript.

Effects of these oligonucleotides on PKC-α mRNA levels is shown in FIG. 6. Oligonucleotides 7008, 3522 and 5352 show reduction of PKC-α mRNA, with 5352 being most active.

A series of 2'-O-propyl chimeric oligonucleotides was synthesized having SEQ ID NO: 3. These oligonucleotides are shown in Table 8.

TABLE 8

Chimeric 2'-O-propyl/deoxy P = S oligonucleotides
bold = 2'-O-propyl; s = P = S linkage, o = P = O linkage

| OLIGO # | SEQUENCE | SEQ ID NO: |
|---|---|---|
| 7199 | AsAsAsAsCsGsTsCsAsGsCsCsAsTsGsGsTsCsCsC | 3 |
| 7273 | AoAoAoAoCoGsTsCsAsGsCsCsAsTsGoGoToCoCoC | 3 |
| 7294 | AsAoAoAoCoGsTsCsAsGsCsCsAsTsGoGoToCoCsC | 3 |
| 7295 | AsAoAoAoCoGsToCsAoGsCoCsAsTsGoGoToCoCsC | 3 |

Figure 7:
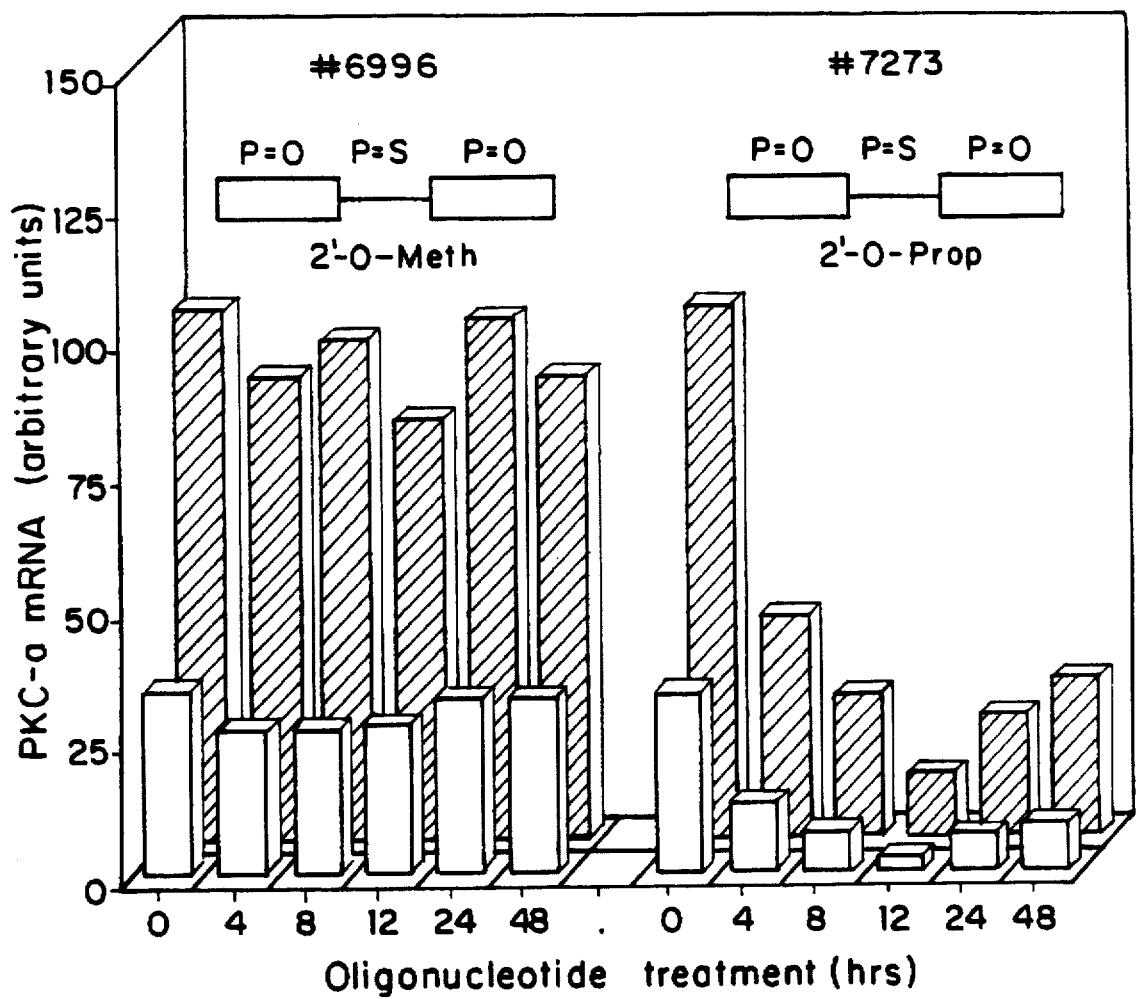
FIG. 7 is a bar graph and diagram showing the effects of several 2'-O-methyl and 2'-O-propyl chimeric oligonucleotides (6996, 7273) of SEQ ID NO: 3 on PKC-α mRNA levels. Hatched bars represent the 8.5 kb transcript, plain bars represent the 4.0 kb transcript.
Figure 8:
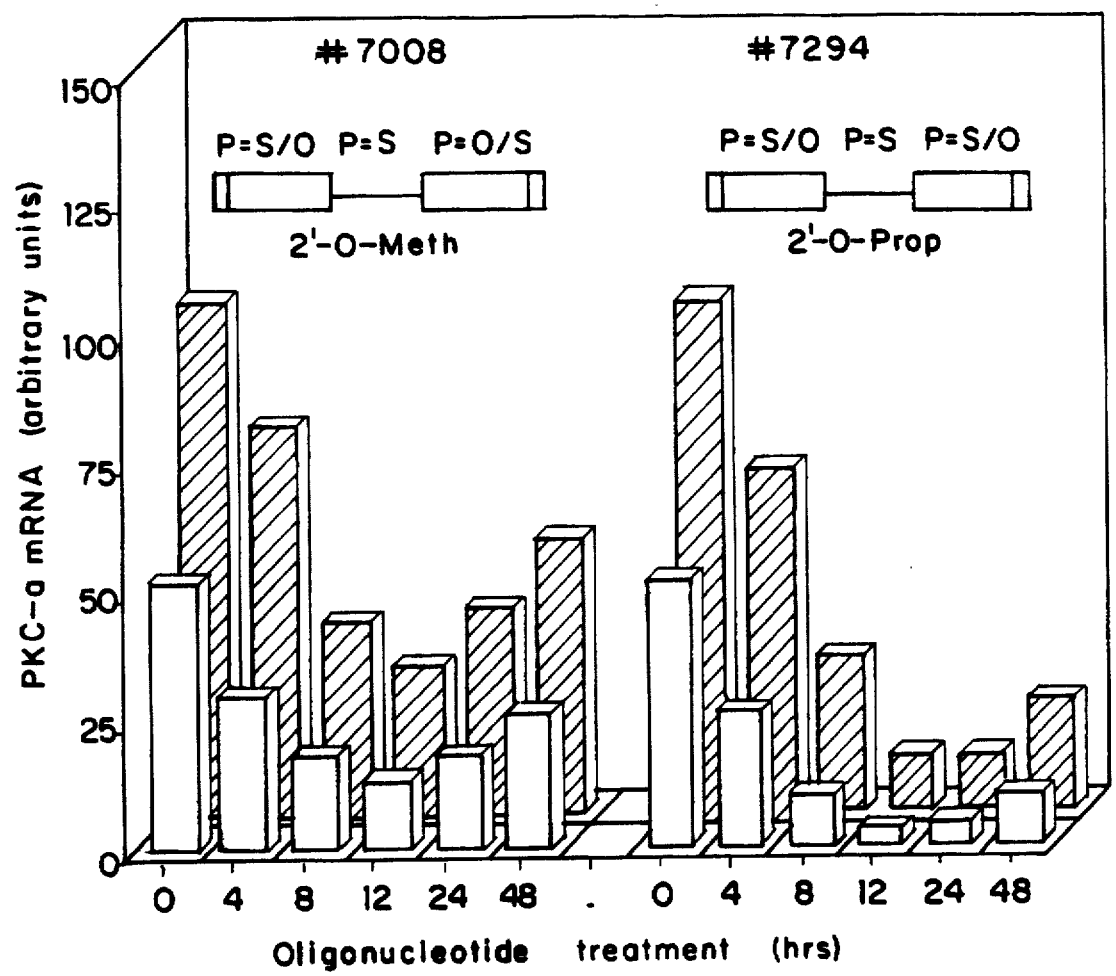
FIG. 8 is a bar graph and diagram showing the effects of additional 2'-O-methyl and 2'-O-propyl chimeric oligonucleotides (7008, 7294) of SEQ ID NO: 3 on PKC-α mRNA levels. Hatched bars represent the 8.5 kb transcript, plain bars represent the 4.0 kb transcript.

These 2'-O-propyl chimeric oligonucleotides were compared to the 2'-O-methyl chimeric oligonucleotides. Oligonucleotides 7273 and 7294 were more active than their 2'-O-methyl counterparts at lowering PKC-α mRNA levels. This is shown in FIGS. 7 and 8.

Example 8

Additional oligonucleotides which decrease PKC-α mRNA:

Additional phosphorothioate oligonucleotides targeted to the human PKC-α 3' untranslated region were designed and synthesized. These sequences are shown in Table 9.

TABLE 9

Chimeric 2'-O-propyl/deoxy P = S oligonucleotides
targeted to PKC-α 3'-UTR
bold = 2'-O-propyl; s = P = S linkage, o = P = O linkage

| OLIGO # | SEQUENCE | SEQ ID NO: |
|---|---|---|
| 6632 | TsTsCs TsCsGs CsTsGs GsTsGs AsGsTs TsTsC | 52 |
| 6653 | TsTsCs TsCsGs CsTsGs GsTsGs AsGsTs TsTsC | 52 |
| 6665 | ToToCo TsCsGs CsTsGs GsTsGs AsGsTo ToToC | 52 |
| 7082 | TsCsTs CsGsCs TsGsGs TsGsAs GsTsTs TsC | 53 |
| 7083 | TsCsTs CsGsCs TsGsGs TsGsAs GsTsTs TsC | 53 |
| 7084 | ToCoTo CsGsCs TsGsGs TsGsAs GsToTo ToC | 53 |

Figure 9A:
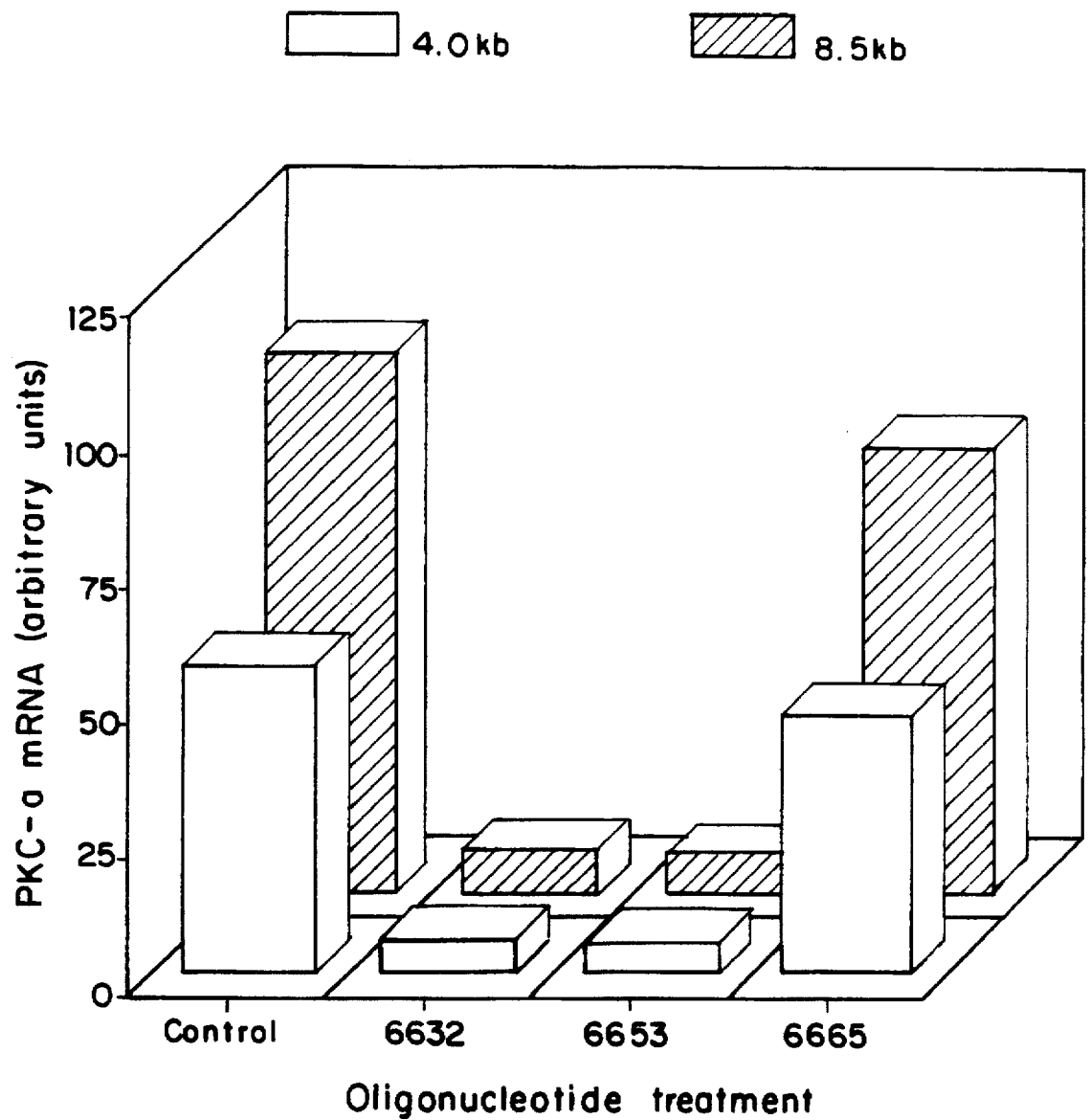
FIG. 9A shows oligonucleotides 6632, 6653 and 6665.
Figure 9B:
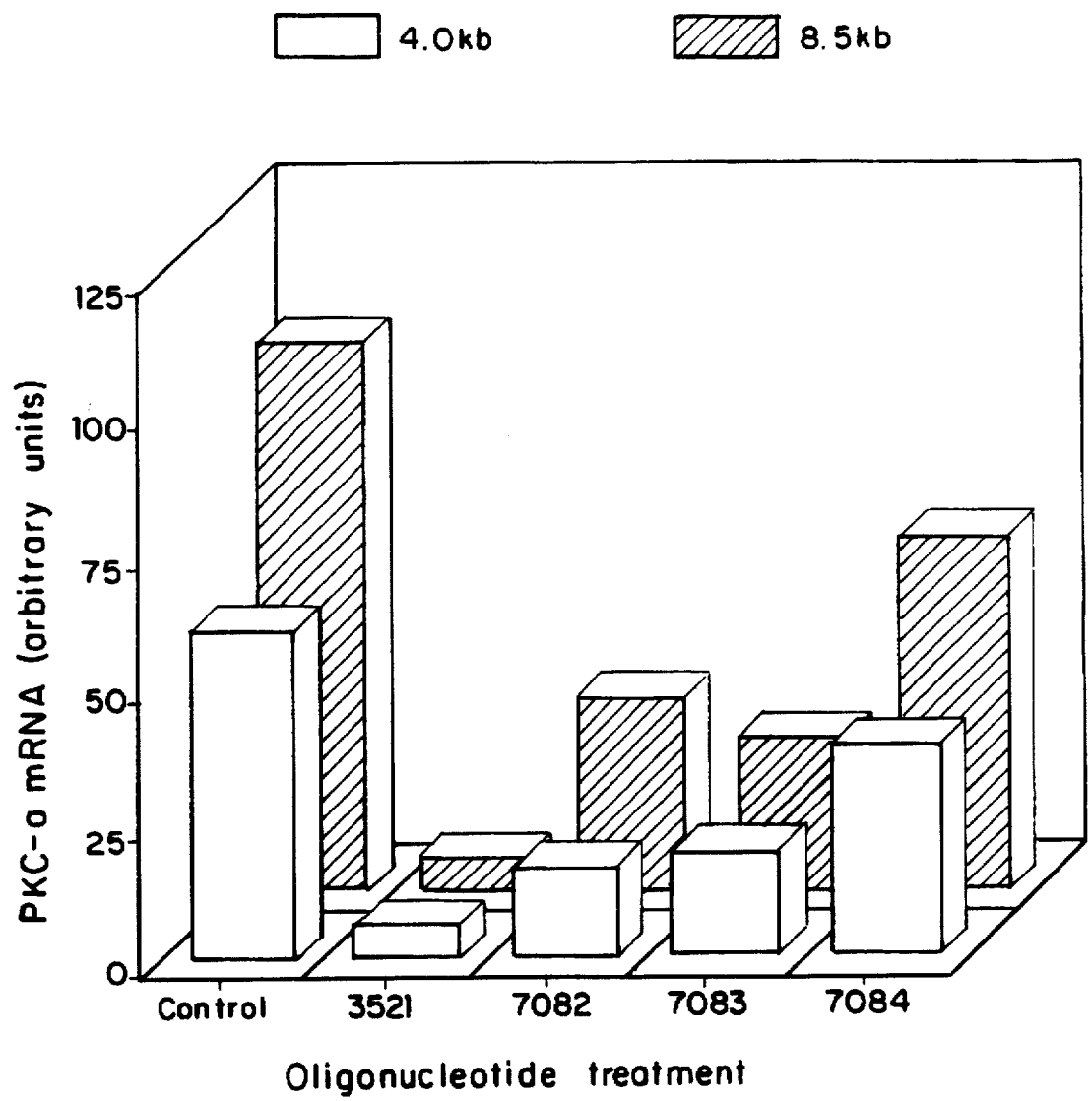
FIG. 9B shows oligonucleotides 3521 (for comparison), 7082, 7083 and 7084. Hatched bars represent the 8.5 kb transcript, plain bars represent the 4.0 kb transcript.

As shown in FIG. 9, oligonucleotides 6632, 6653, 7082 and 7083 are most active in reducing PKC-α mRNA levels.

Example 9

Culture of human A549 lung tumor cells:

The human lung carcinoma cell line A549 was obtained from the American Type Culture Collection (Bethesda Md.). Cells were grown in Dulbecco's Modified Eagle's Medium (Irvine Scientific, Irvine Calif.) containing 1 gm glucose/ liter and 10% fetal calf serum (Irvine Scientific). Cells were trypsinized and washed and resuspended in the same medium for introduction into mice.

Example 10

Effect of ISIS 3521 on the growth of human A549 tumor cells in nude mice:

200 μl of A549 cells ($5\times10^6$ cells) were implanted subcutaneously in the inner thigh of nude mice. ISIS 3521, a phosphorothioate oligonucleotide with Sequence ID NO 2 was administered twice weekly for four weeks, beginning one week following tumor cell inoculation. Oligonucleotides were formulated with cationic lipids (DMRIE/DOPE) and given subcutaneously in the vicinity of the tumor. Oligonucleotide dosage was 5 mg/kg with 60 mg/kg cationic lipid. Tumor size was recorded weekly.

Figure 10:
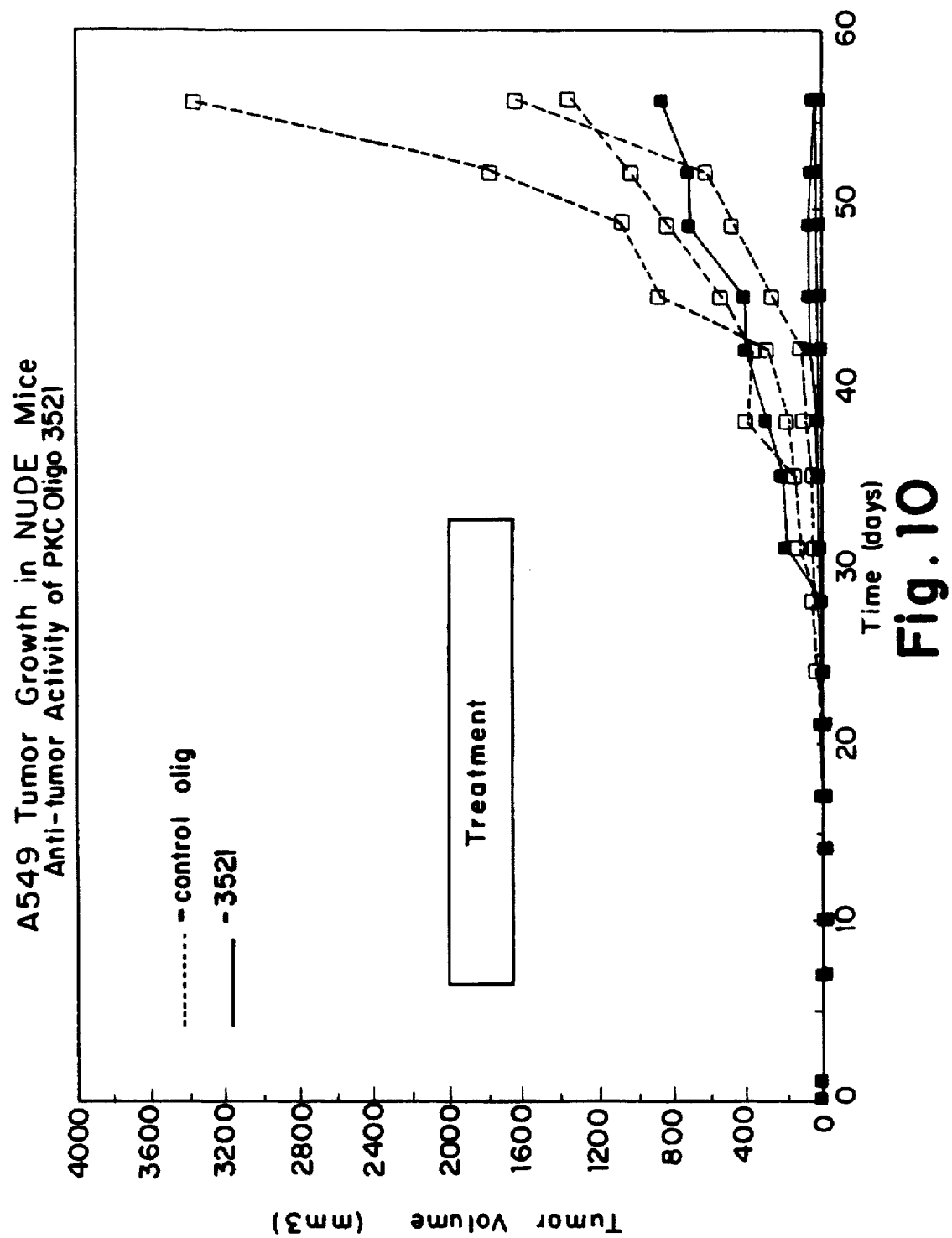
FIG. 10 is a line graph showing anti-tumor activity of ISIS 3521. Each dashed line represents tumor volume in one animal treated with control oligonucleotide; each solid line represents tumor volume in one animal treated with ISIS 3521.

As shown in FIG. 10, tumor growth was almost completely inhibited in two of the three mice, and reduced compared to control in the third mouse. This inhibition of tumor growth by ISIS 3521 is statistically significant. The control oligonucleotide (ISIS 1082) is a 21-mer phosphorothioate oligonucleotide without significant sequence homology to the PKC mRNA target.

Administration of oligonucleotides to mice whose tumors had already reached detectable size had no discernable effect on subsequent tumor growth.

Example 11

Figure 11A:
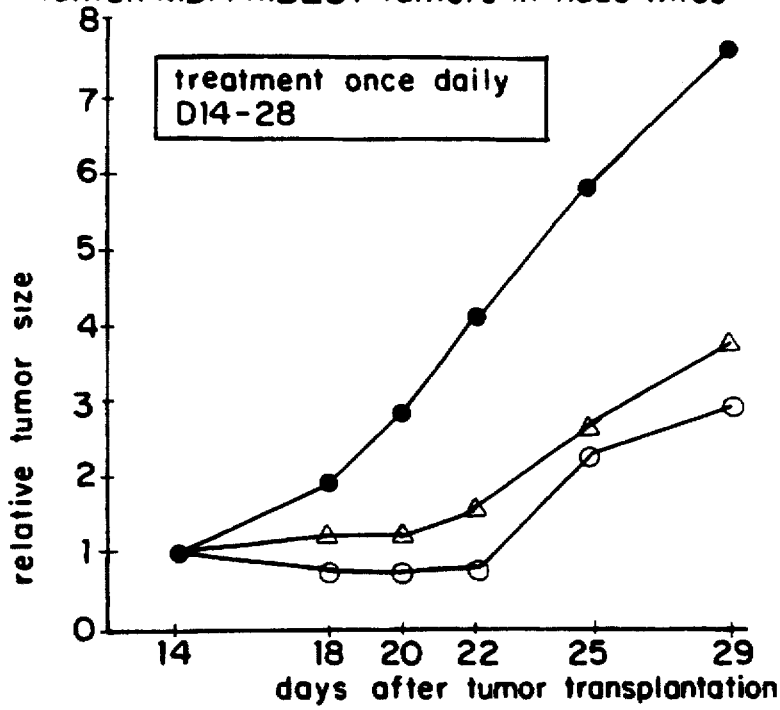
FIG. 11A shows results obtained with ISIS 3521.
Figure 11B:
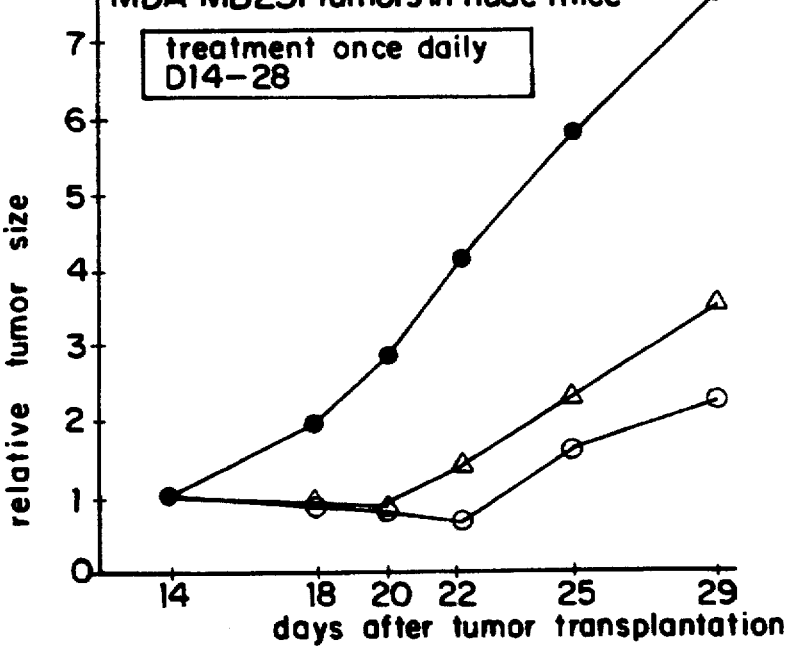
FIG. 11B shows results obtained with ISIS3527. Each line represents tumor volume in one animal. •=control; ○=oligonucleotide at 60 mg/kg; Δ=oligonucleotide at 6 mg/kg.

Effect of antisense oligonucleotides on growth of human MDA-MB231 tumors in nude mice:

MDA-MB231 human breast carcinoma cells were obtained from the American Type Culture Collection (Bethesda, Md.). Serially transplanted MDA-MB231 tumors were established subcutaneously in nude mice. Beginning two weeks later, oligonucleotides 3521 and 3527, a phosphorothioate oligonucleotide having Sequence ID NO. 5, in saline, were administered intravenously daily for 14 days at dosages of 60 mg/kg and 6 mg/kg. Control oligonucleotide ISIS 1082 was also administered at these doses, and a saline control was also given. Tumor growth rates were monitored for the two-week period of oligonucleotide administration. As shown in FIG. 11, both PKC-α oligonucleotides (3521 and 3527) significantly inhibit tumor growth at dosages of 60 mg/kg and 6 mg/kg. The control oligonucleotide (ISIS 1082) also showed some reduction in tumor growth, but this effect was less than with antisense oligonucleotides even at high doses, and considerably less at the lower dose. A lower-dose study was conducted using the same oligonucleotides at 6 mg/kg and 0.6 mg/kg. At 0.6 mg/kg ISIS 3521 significantly reduced tumor growth. At this concentration, ISIS 3527 also reduced tumor growth, but this result was not statistically significant.

Example 12

Effect of oligonucleotides on the growth of murine Lewis lung carcinoma in mice:

Serially transplanted murine Lewis lung carcinomas were established in mice. Oligonucleotides 3521 and 3527 were administered intravenously every day for 14 days at doses of 6 mg/kg and 0.6 mg/kg. Tumor growth rates were monitored for the two-week period of oligonucleotide administration. As expected, these oligonucleotides, which are targeted to human PKC sequences, had insignificant effects on the mouse-derived tumors.

Example 13

Effects of antisense oligonucleotide ISIS 4189 on endogenous PKC-α expression in hairless mice:

In order to study oligonucleotide effects on endogenous PKC mRNA levels in normal animals, it was necessary to employ an oligonucleotide complementary to the murine PKC-α. ISIS 4189 is a 20-mer phosphorothioate oligonucleotide targeted to the AUG codon of mouse PKC-α. This region is without homology to the human PKC sequence and the oligonucleotide has no effect on expression of PKC-α in human cells. ISIS 4189 has an IC50 of 200 nM for mRNA reduction in C127 mouse breast epithelial cells. ISIS 4189 in saline was administered intraperitoneally to hairless mice at concentrations of 1, 10 or 100 mg/kg body weight. Injections were given daily for seven days. Tissues from liver, kidney, spleen, lung and skin were removed and PKC-α mRNA and protein levels were determined. Histopathological examination was also performed on liver, kidney and lung samples. ISIS 4189 at 100 mg/kg inhibited endogenous PKC-α mRNA levels in the mouse liver to 10–15% of control (saline) levels.

Example 14

Screening of antisense oligonucleotides complementary to human PKC-η:

A series of 20-mer phosphorothioate oligonucleotides complementary to human PKC-η were synthesized. These oligonucleotides were screened at a concentration of 500 nM for ability to decrease PKC-η mRNA levels in human A549 cells, using a Northern blot assay. The oligonucleotide sequences are shown in Table 10 and the results are shown in FIG. 12.

TABLE 10

OLIGONUCLEOTIDES TARGETED TO HUMAN PKC-η mRNA

| SEQ ID | Sequence | | | | | | | Target | SEQ ID |
|---|---|---|---|---|---|---|---|---|---|
| 6431 | CGA | CAT | GCC | GGC | GCC | GCT | GC | AUG | 40 |
| 6442 | CAG | ACG | ACA | TGC | CGG | CGC | CG | AUG | 41 |
| 6443 | GCC | TGC | TTC | GCA | GCG | GGA | GA | 5' UTR | 42 |
| 6432 | ACA | GGT | GCA | GGA | GTC | GAG | GC | 5' UTR | 43 |
| 6433 | GTC | CCG | TCT | CAG | GCC | AGC | CC5' | UTR | 44 |
| 6435 | CCT | CAC | CGA | TGC | GGA | CCC | TC | Coding | 45 |
| 6441 | ATT | GAA | CTT | CAT | GGT | GCC | AG | Coding | 46 |
| 6581 | TCT | CAC | TCC | CCA | TAA | GGC | TA | 3' UTR | 47 |
| 6580 | TTC | CTT | TGG | GTT | CTC | GTG | CC | 3' UTR | 48 |
| 6436 | AAC | TCG | AGG | TGG | CCG | CCG | TC | Coding | 54 |
| 6434 | CGC | CTT | CGC | ATA | GCC | CTT | TG | Coding | 55 |
| 6444 | GGA | AGG | GGT | GAT | TGC | GGG | CC | Coding | 56 |
| 6445 | AAC | ACG | CCC | ATT | GCC | CAC | CA | Coding | 57 |
| 6446 | GTC | TCA | AGA | TGG | CGT | GCT | CG | Coding | 58 |
| 6553 | GCG | ATG | GTT | CAG | CTG | GGC | CC | Coding | 59 |
| 6605 | GCC | CTC | TCT | CTC | ACT | CCC | CA | 3' UTR | 60 |
| 6579 | CTG | GGA | AGG | TCC | GAT | AGA | GG | 3' UTR | 61 |
| 6603 | AAG | GCT | GAT | GCT | GGG | AAG | GT | 3' UTR | 62 |

Oligonucleotides 6432, 6443, 6431, 6442, 6435, 6434, 6445, 6553, 6581 and 6603 reduced PKC-η mRNA levels by greater than 50%. The most potent oligonucleotides were ISIS 6581 (targeting 3' untranslated region) and ISIS 6445 (targeting coding region) which gave nearly complete loss of PKC mRNA in this assay.

What is claimed is:

1. An isolated and purified oligonucleotide consisting of a nucleotide sequence selected from the group consisting of SEQ ID NO: 2 and SEQ ID NO: 5.

2. The oligonucleotide of claim 1 wherein at least one nucleotide comprises a phosphorothioate linkage.

3. The oligonucleotide of claim 1 wherein at least one nucleotide comprises a 2'-modified sugar.

4. The oligonucleotide of claim 3 wherein the modification is a 2'-O-alkyl or 2'-fluoro modification.

5. The oligonucleotide of claim 3 wherein the modification is a 2'-O-methyl or 2'-O-propyl modification.

6. A pharmaceutical composition comprising the oligonucleotide of claim 1 and a pharmaceutically acceptable carrier or diluent.

7. An isolated and purified oligonucleotide consisting of SEQ ID NO: 2, wherein said oligonucleotide hybridizes to DNA or RNA encoding human protein kinase C and reduces human protein kinase C expression.

8. The oligonucleotide of claim 7 wherein at least one nucleotide comprises a phosphorothioate linkage.

9. The oligonucleotide of claim 7 wherein at least one nucleotide comprises a 2'-modified sugar.

10. The oligonucleotide of claim 9 wherein the modification is a 2'-O-alkyl or 2'-fluoro modification.

11. The oligonucleotide of claim 9 wherein the modification is a 2'-O-methyl or 2'-O-propyl modification.

12. An isolated and purified oligonucleotide consisting of SEQ ID NO: 3, wherein said oligonucleotide hybridizes to DNA or RNA encoding human protein kinase C and reduces human protein kinase C expression, wherein the $IC_{50}$ is 1 µM or less.

13. The oligonucleotide of claim 12 wherein at least one nucleotide comprises a phosphorothioate linkage.

14. The oligonucleotide of claim 12 wherein at least one nucleotide comprises a 2'-modified sugar.

15. The oligonucleotide of claim 14 wherein the modification is a 2'-O-alkyl or 2'-fluoro modification.

16. The oligonucleotide of claim 14 wherein the modification is a 2'-O-methyl or 2'-O-propyl modification.

17. An isolated and purified oligonucleotide consisting of SEQ ID NO: 5, wherein said oligonucleotide hybridizes to DNA or RNA encoding human protein kinase C and reduces human protein kinase C expression.

18. The oligonucleotide of claim 17 wherein at least one nucleotide comprises a phosphorothioate linkage.

19. The oligonucleotide of claim 17 wherein at least one nucleotide comprises a 2'-modified sugar.

20. The oligonucleotide of claim 19 wherein the modification is a 2'-O-alkyl or 2'-fluoro modification.

21. The oligonucleotide of claim 19 wherein the modification is a 2'-O-methyl or 2'-O-propyl modification.

* * * * *